United States Patent
Robbins et al.

(10) Patent No.: US 9,494,799 B2
(45) Date of Patent: Nov. 15, 2016

(54) WAVEGUIDE EYE TRACKING EMPLOYING SWITCHABLE DIFFRACTION GRATINGS

(71) Applicant: MICROSOFT TECHNOLOGY LICENSING, LLC, Redmond, WA (US)

(72) Inventors: Steven Robbins, Redmond, WA (US); Ian A. Nguyen, Renton, WA (US)

(73) Assignee: MICROSOFT TECHNOLOGY LICENSING, LLC, Redmond, WA (US)

(*) Notice: Subject to any disclaimer, the term of this patent is extended or adjusted under 35 U.S.C. 154(b) by 110 days.

(21) Appl. No.: 14/495,273

(22) Filed: Sep. 24, 2014

(65) Prior Publication Data

US 2016/0085300 A1    Mar. 24, 2016

(51) Int. Cl.
| | |
|---|---|
| G02B 27/01 | (2006.01) |
| G06F 3/01 | (2006.01) |
| G02B 27/00 | (2006.01) |
| G02F 1/29 | (2006.01) |
| H04N 5/33 | (2006.01) |
| H04N 5/232 | (2006.01) |
| G06T 19/00 | (2011.01) |

(Continued)

(52) U.S. Cl.
CPC ....... *G02B 27/0172* (2013.01); *G02B 27/0093* (2013.01); *G02B 27/0101* (2013.01); *G02F 1/292* (2013.01); *G06F 3/013* (2013.01); *G06T 19/006* (2013.01); *H04N 5/23212* (2013.01); *H04N 5/33* (2013.01); *A61B 3/005* (2013.01); *A61B 3/113* (2013.01); *G02B 13/14* (2013.01); *G02B 2027/014* (2013.01); *G02B 2027/0138* (2013.01); *G02B 2027/0178* (2013.01)

(58) Field of Classification Search
None
See application file for complete search history.

(56) References Cited

U.S. PATENT DOCUMENTS

| | | |
|---|---|---|
| 3,861,784 A | 1/1975 | Torok |
| 4,235,504 A | 11/1980 | Ikeda et al. |

(Continued)

FOREIGN PATENT DOCUMENTS

| | | |
|---|---|---|
| CA | 1174882 A1 | 9/1984 |
| EP | 2290428 A2 | 2/2011 |

(Continued)

OTHER PUBLICATIONS

Office Action dated Nov. 19, 2015, in U.S. Appl. No. 14/140,987, filed Dec. 26, 2013.

(Continued)

*Primary Examiner* — Mike Stahl
(74) *Attorney, Agent, or Firm* — Daniel Choi; Micky Minhas

(57) ABSTRACT

A transparent waveguide, for use in tracking an eye illuminated by infrared light, includes an input-coupler and an output-coupler. The input-coupler includes a stack of electronically switchable diffractive gratings arranged parallel to one another, each of which has a respective lens power that causes each of the gratings in the stack to have a different focal length. Each grating, when turned on, couples received infrared light into the waveguide. A sensor images an eye in dependence on infrared light beams that exit the waveguide at the output-coupler. Images of an eye, obtained using the sensor, are analyzed to determine which one of the electronically switchable diffractive gratings, when turned on, provides a best focused image of the eye or portion thereof. The one of the electronically switchable diffractive gratings, which provides the best focused image of the eye, is used for imaging the eye during eye tracking.

20 Claims, 14 Drawing Sheets

(51) Int. Cl.
*G02B 13/14* (2006.01)
*A61B 3/00* (2006.01)
*A61B 3/113* (2006.01)

(56) References Cited

U.S. PATENT DOCUMENTS

| | | |
|---|---|---|
| 4,711,512 A | 12/1987 | Upatnieks |
| 5,383,042 A | 1/1995 | Robinson |
| 5,440,669 A | 8/1995 | Rakuljic et al. |
| 5,491,570 A | 2/1996 | Rakuljic et al. |
| 5,596,451 A | 1/1997 | Handschy et al. |
| 5,614,988 A | 3/1997 | Kato et al. |
| 5,701,132 A | 12/1997 | Kollin et al. |
| 5,856,842 A | 1/1999 | Tedesco |
| 5,886,822 A | 3/1999 | Spitzer |
| 5,966,223 A | 10/1999 | Friesem et al. |
| 5,986,746 A | 11/1999 | Metz et al. |
| 6,285,813 B1 | 9/2001 | Schultz et al. |
| 6,323,970 B1 | 11/2001 | Popovich |
| 6,529,331 B2 | 3/2003 | Massof |
| 6,580,529 B1 | 6/2003 | Amitai et al. |
| 6,791,760 B2 | 9/2004 | Janeczko et al. |
| 6,804,066 B1 | 10/2004 | Ha et al. |
| 7,184,615 B2 | 2/2007 | Levola |
| 7,190,859 B2 | 3/2007 | Greiner et al. |
| 7,205,960 B2 | 4/2007 | David |
| 7,283,705 B2 | 10/2007 | Paek et al. |
| 7,401,920 B1 | 7/2008 | Kranz et al. |
| 7,576,916 B2 | 8/2009 | Amitai |
| 7,619,739 B1 | 11/2009 | Sutherland et al. |
| 7,660,047 B1 | 2/2010 | Travis et al. |
| 7,907,342 B2 | 3/2011 | Simmonds et al. |
| 8,068,709 B2 | 11/2011 | Iazikov et al. |
| 8,160,411 B2 | 4/2012 | Levola et al. |
| 8,233,204 B1 | 7/2012 | Robbins et al. |
| 8,432,589 B2 | 4/2013 | Tompkin et al. |
| 8,487,838 B2 | 7/2013 | Lewis et al. |
| 8,611,014 B2 | 12/2013 | Valera et al. |
| 8,638,498 B2 | 1/2014 | Bohn et al. |
| 8,817,350 B1 | 8/2014 | Robbins et al. |
| 2003/0184868 A1 | 10/2003 | Geist |
| 2005/0105084 A1 | 5/2005 | Wang et al. |
| 2006/0132914 A1 | 6/2006 | Weiss et al. |
| 2007/0041684 A1 | 2/2007 | Popovich et al. |
| 2008/0129530 A1 | 6/2008 | Lokos |
| 2009/0128901 A1 | 5/2009 | Tilleman |
| 2009/0323737 A1 | 12/2009 | Ensher et al. |
| 2010/0079865 A1 | 4/2010 | Saarikko et al. |
| 2010/0149073 A1 | 6/2010 | Chaum et al. |
| 2010/0157400 A1 | 6/2010 | Dimov et al. |
| 2011/0037951 A1 | 2/2011 | Hua et al. |
| 2011/0109528 A1 | 5/2011 | Mun et al. |
| 2011/0122305 A1 | 5/2011 | Kobayashi |
| 2012/0017153 A1 | 1/2012 | Matsuda et al. |
| 2012/0038918 A1 | 2/2012 | Liu et al. |
| 2012/0081769 A1 | 4/2012 | Dergachev |
| 2012/0120493 A1 | 5/2012 | Simmonds et al. |
| 2012/0236030 A1 | 9/2012 | Border |
| 2013/0077049 A1 | 3/2013 | Bohn |
| 2013/0101253 A1 | 4/2013 | Popovich et al. |
| 2013/0222384 A1 | 8/2013 | Futterer |
| 2013/0250431 A1 | 9/2013 | Robbins et al. |
| 2013/0278631 A1 | 10/2013 | Border et al. |
| 2013/0286178 A1 | 10/2013 | Lewis et al. |
| 2013/0300637 A1 | 11/2013 | Smits et al. |
| 2013/0314793 A1 | 11/2013 | Robbins et al. |
| 2014/0010265 A1 | 1/2014 | Peng |
| 2014/0016051 A1 | 1/2014 | Kroll et al. |
| 2014/0044143 A1 | 2/2014 | Clarkson et al. |
| 2014/0098010 A1 | 4/2014 | Travis |
| 2014/0104665 A1 | 4/2014 | Popovich et al. |
| 2014/0140653 A1 | 5/2014 | Brown et al. |
| 2014/0140654 A1 | 5/2014 | Brown et al. |
| 2014/0184699 A1 | 7/2014 | Ito et al. |
| 2014/0204455 A1 | 7/2014 | Popovich et al. |
| 2014/0211322 A1 | 7/2014 | Bohn et al. |
| 2014/0361957 A1 | 12/2014 | Hua et al. |
| 2015/0185475 A1 | 7/2015 | Saarikko et al. |
| 2015/0289762 A1 | 10/2015 | Popovich et al. |

FOREIGN PATENT DOCUMENTS

| | | |
|---|---|---|
| JP | 61-213802 | 9/1986 |
| WO | 2007054928 A1 | 5/2007 |
| WO | 2010057219 A1 | 5/2010 |
| WO | 2013049012 A1 | 4/2013 |
| WO | 2013163347 A1 | 10/2013 |
| WO | 2013167864 A1 | 11/2013 |
| WO | 2013175465 A1 | 11/2013 |

OTHER PUBLICATIONS

Response to Office Action filed Oct. 6, 2015, in U.S. Appl. No. 14/140,987, filed Dec. 26, 2013.
English Abstract of Japanese Patent No. JP61213802 published Sep. 22, 1986.
Office Action dated Oct. 14, 2015 in U.S. Appl. No. 14/456,512, filed Aug. 11, 2014.
International Search Report and Written Opinion mailed Oct. 29, 2015 in PCT Application No. PCT/US2015/044400 filed Aug. 10, 2015.
International Search Report and Written Opinion mailed Nov. 26, 2015 in PCT Application No. PCT/US2015/050066 filed Sep. 15, 2015.
Office Action dated Jan. 7, 2015, in U.S. Appl. No. 14/140,987, filed Dec. 26, 2013.
"International Search Report and Written Opinion Issued in PCT Application No. PCT/US2015/050316", Mailed Date: Jan. 14, 2016, 12 Pages.
Response to Office Action filed Feb. 19, 2016 in U.S. Appl. No. 14/140,987, 17 pages.
Response to Office Action filed Jan. 14, 2016 in U.S. Appl. No. 14/1456,512, 17 pages.
Notice of Allowance dated Mar. 2, 2016, in U.S. Appl. No. 14/456,512, filed Aug. 11, 2014.
Massenot et al., "Multiplexed Holographic Transmission Gratings Recorded in Holographic Polymer-Dispersed Liquid Crystals: Static and Dynamic Studies", Applied Optics, vol. 44, Issue 25, Sep. 2005.
Zharkova et al., "Study of the Dynamics of Transmission Gratings Growth on Holographic Polymer-Dispersed Liquid Crystals", International Conference on Methods of Aerophysical Research, ICMAR, Aug. 2008.
Yan et al., "Multiplexing Holograms in the Photopolymer with Equal Diffraction Efficiency," Advances in Optical Data Storage Technology, Proceedings of SPIE, vol. 5643, (SPIE, Bellingham, WA), Jan. 2005.
Pu et al., "Exposure Schedule for Multiplexing Holograms in Photopolymer Films," Opt. Eng. 35(10), Oct. 1996.
Han et al., "Accurate Diffraction Efficiency Control for Multiplexed Volume Holographic Gratings", Opt. Eng. 41, Nov. 2002.
Minier et al., "Diffraction Characteristics of Superimposed Holographic Gratings in Planar Optical Waveguides", IEEE Photonics Technology Letters, vol. 4, No. 10, Oct. 1992.
Kress et al., "Exit Pupil Expander for Wearable See-Through Displays", Photonic Applications for Aerospace, Transportation, and Harsh Environment III, Proc. of SPIE vol. 8368, 83680D, May 1, 2012.
International Search Report and Written Opinion dated Mar. 18, 2015, in International Patent Application No. PCT/US2014/066999 filed Nov. 24, 2014.
Amendment dated Apr. 7, 2015, in U.S. Appl. No. 14/140,987, filed Dec. 26, 2013.
Iwamoto, Kazuyo, et al., "Eye Movement Tracking Type Image Display System for Wide Image Presentation with High-resolution-Evaluation of High-resolution Image Presentation," Proceedings of the 2002 IEEE/RSJ Intl. Conference on Intelligent Robots and Systems EPFL, Oct. 2002, 6 pages.

(56) References Cited

OTHER PUBLICATIONS

Mukawa et al., "8.4: Distinguished Paper: A Full Color Eyewear Display using Holographic Planar Waveguides", Information Technology Laboratories, Sony Corporation, Tokyo, Japan, May 2008, SID 08 Digest pp. 89-92.
U.S. Appl. No. 14/140,987, filed Dec. 26, 2013.
Office Action dated Feb. 28, 2014, in U.S. Appl. No. 14/140,987, filed Dec. 26, 2013.
Amendment dated May 15, 2014, in U.S. Appl. No. 14/140,987, filed Dec. 26, 2013.
U.S. Appl. No. 14/456,512, filed Aug. 11, 2014.
U.S. Appl. No. 14/487,404, filed Sep. 16, 2014.
Honig, Zach, "Vuzix Designs Smart Glasses to Look Like Sunshades, Tout Connected Transparent Display", Published on: Jan. 7, 2012, Available at: http://www.engadget.com/2012/01/07/vuzix-smart-glasses-ces-2012/.
Amendment dated Dec. 3, 2014, in U.S. Appl. No. 14/140,987, filed Dec. 26, 2013.
Amendments under Article 34 PCT dated Feb. 29, 2016, International Application No. PCT/US2015/050066.
Response to International Search Report and Written Opinion filed Apr. 28, 2016, in International Patent Application No. PCT/US2015/050316.
Notice of Allowance dated Jun. 3, 2016 in U.S. Appl. No. 14/140,987.
Second Written Opinion Issued mailed Aug. 2, 2016, in PCT Application No. PCT/US2015/050316 filed Sep. 16, 2015.

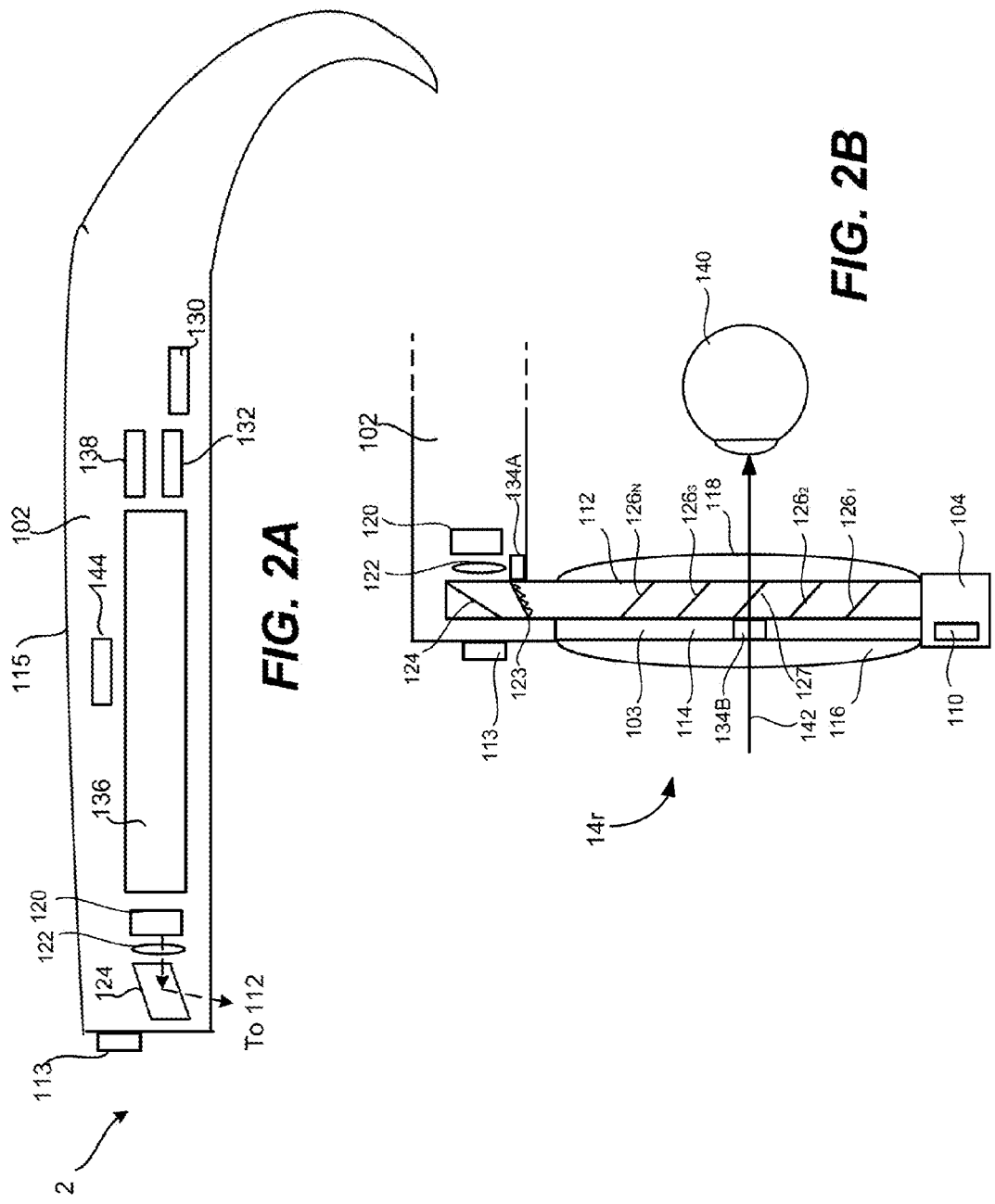

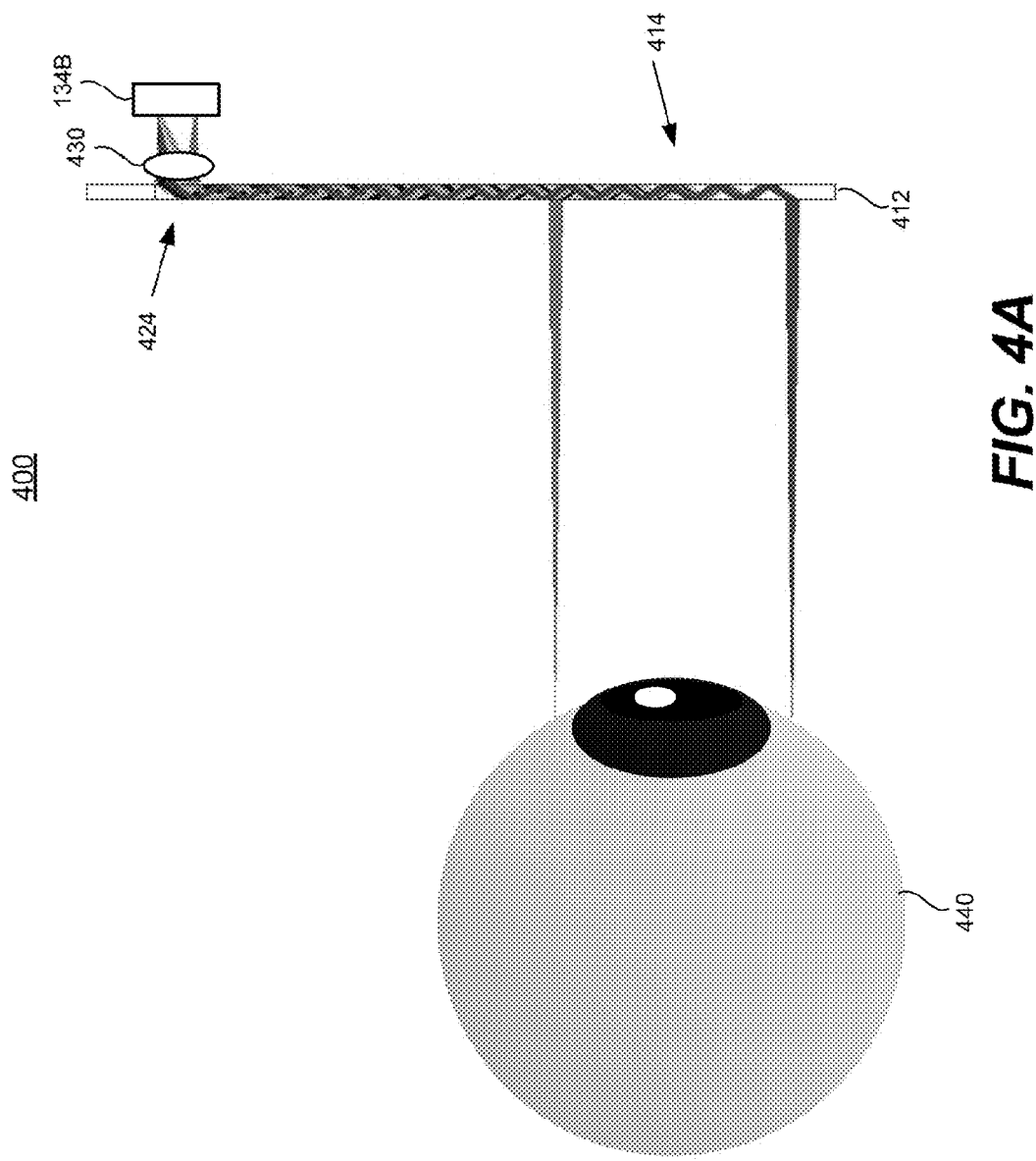

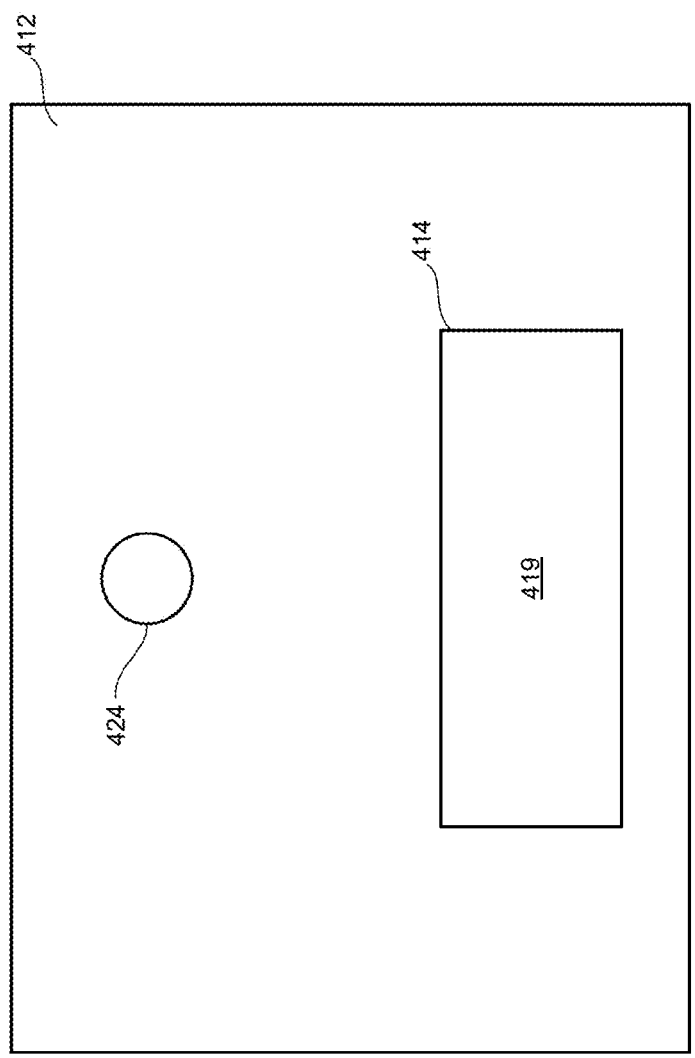

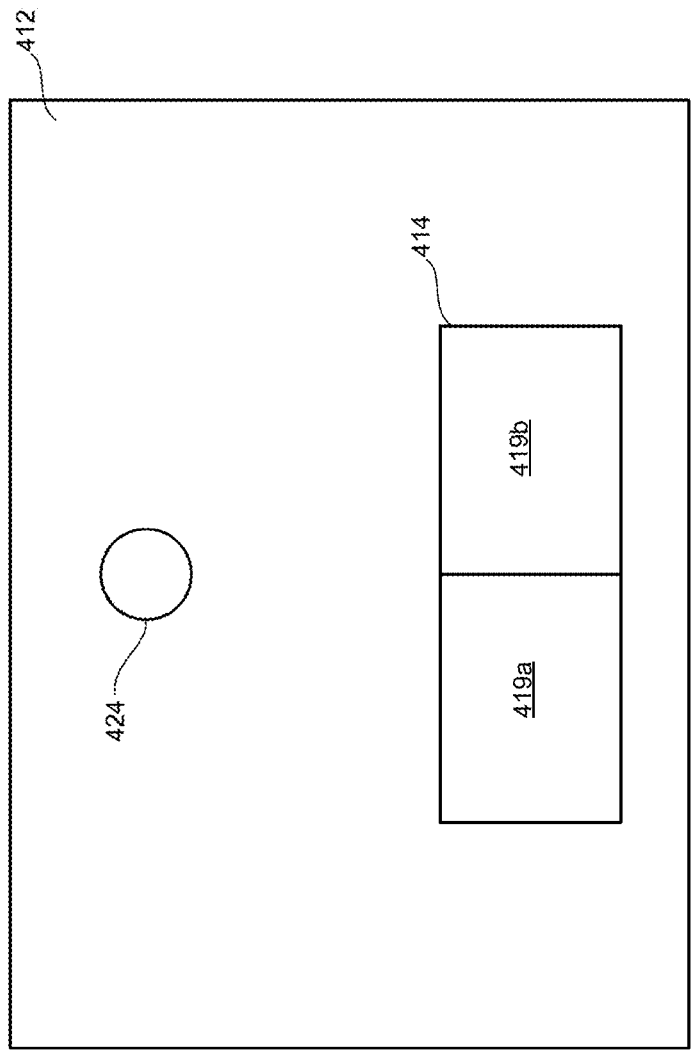

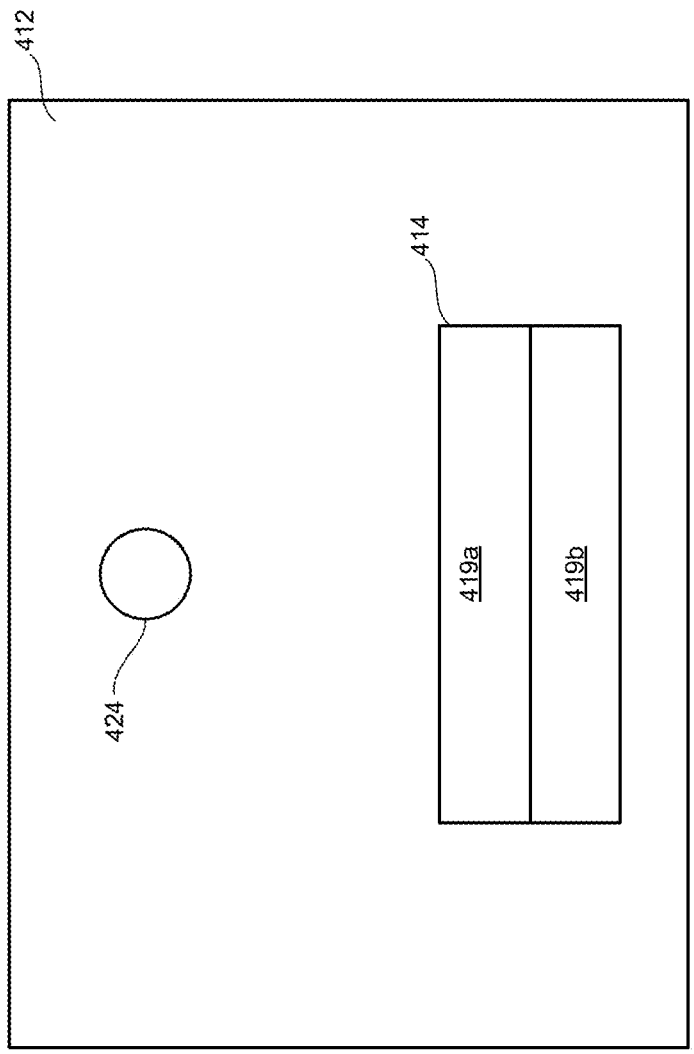

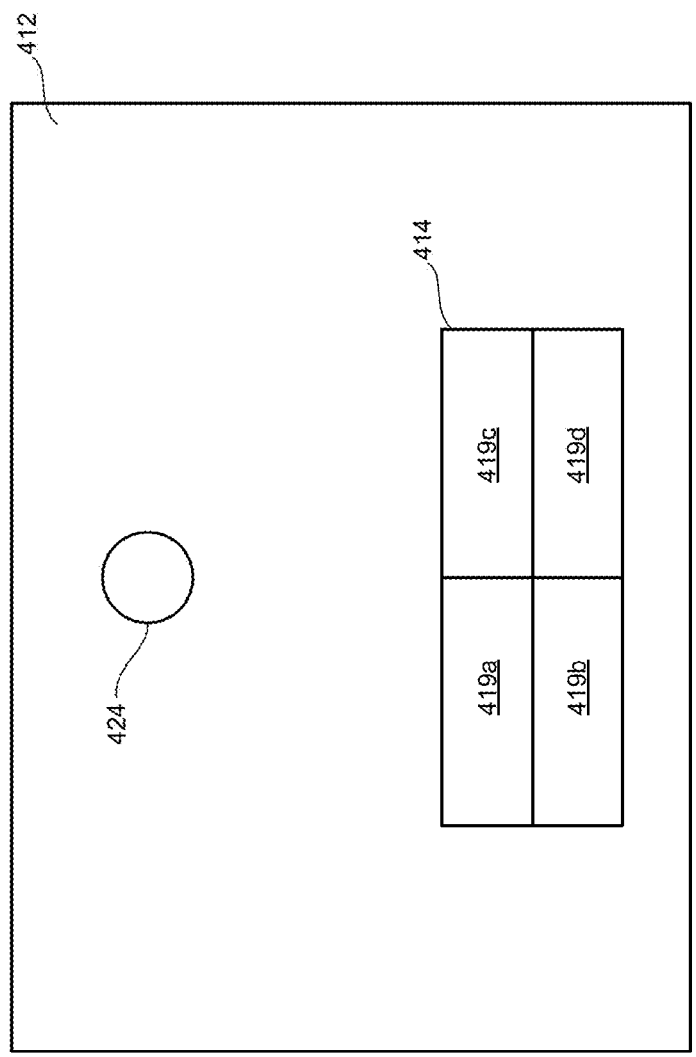

WAVEGUIDE EYE TRACKING EMPLOYING SWITCHABLE DIFFRACTION GRATINGS

BACKGROUND

A see-through, mixed reality display device system enables a user to observe digital information overlaid on the physical scenery. To enable hands-free user interaction, a see-through, mixed reality display device system may further be equipped with an eye tracker. Typically, an eye tracker includes an infrared (IR) light source to illuminate the user's eye and a sensor (e.g., camera) to image the user's eye, e.g., to observe the reflected glints and iris movements for calculation of a gaze direction. The illumination and the imaging of the eye are preferably implemented such that: the see-through properties of the mixed reality display device system are not impaired by the eye tracking hardware; imaging of the eye works with all types of prescription spectacles; and imaging of the eye covers the entire eye movement range plus an inter-pupillary distance range and an eye relief distance range.

One way to image an eye for eye tracking is using a simple camera mounted on the frame of a head mounted display (HMD) device, wherein the camera is directly focused on the user's eye. In other words, there is a direct line of sight from the camera to the eye. While such a configuration is relatively simple and inexpensive, it is highly sensitive to the position and movement of the camera relative to the eye. Also, with such a configuration the camera needs to be positioned close to the eye level, which typically causes at least partial obstruction of the see-through properties of the mixed reality display device system. Alternatively, a partial reflector may be used to fold the camera view path to the user's temple. While this alternative configuration allows the camera to be positioned outside the see-through field, implementation of this alternative configuration is problematic if the eye tracking needs to work with prescription eyewear.

Another possibility is to use a reverse optical path imaging in a free form prism or other eyepiece based mixed reality display device system. This technique relies on the actual display optics to also provide the imaging functionality for eye tracking. However, because components of a free form prism or eyepiece tend to be rather large in size, this approach is not always practical. Adding a free form optical element for eye tracking only is also possible, but this would be expensive and would add significant weight and size to the system.

SUMMARY

Certain embodiments described herein relate to a waveguide that is for use in tracking an eye that is illuminated by infrared light. Such a waveguide, which can be used in a head mounted display (HMD), but is not limited for use therewith, is transparent and includes an input-coupler and an output-coupler. In accordance with specific embodiments, the input-coupler comprises a stack of two or more electronically switchable diffractive gratings arranged parallel to one another. Each of the electronically switchable diffractive gratings has a respective lens power and a respective prismatic power. The lens power of each of the electronically switchable diffractive gratings differ from one another such that each of the electronically switchable diffractive gratings has a different focal length. Each of the electronically switchable diffractive gratings, when turned on, is adapted to receive infrared light having the infrared wavelength and couple the received infrared light into the waveguide. When the input-coupler is positioned in front of an eye that is illuminated with the infrared light, at least a portion of the infrared light reflected from the eye and received by the input-coupler is coupled into the waveguide at the input-coupler, propagates within the waveguide from the input-coupler to the output-coupler by way of total internal reflections, and exits the waveguide proximate the output-coupler. A sensor images an eye in dependence on infrared light beams that exit the waveguide at the output-coupler. In certain embodiments, a lens module is between the output-coupler and the sensor, and the infrared light beams that exit the waveguide at the output-coupler pass through the lens module before being incident on the sensor.

An input-coupler controller controls when each of the electronically switchable diffractive gratings is turned on, such that only one of the electronically switchable diffractive gratings is turned on at a time. An image analyzer analyzes two or more images of an eye, obtained using the sensor, to determine which one of the electronically switchable diffractive gratings, when turned on, provides a best focused image of an eye or portion thereof. The input-coupler controller causes the one of the electronically switchable diffractive gratings, which the image analysis module determines provides the best focused image of the eye, to be used for imaging the eye during eye tracking.

In certain embodiments, the input-coupler also includes a second stack of two or more electronically switchable diffractive gratings arranged parallel to one another, wherein the second stack being adjacent to the first stack. In such an embodiment, the electronically switchable diffractive gratings in the second stack provide a field-of-view that differs from the field-of-view provided by the electronically switchable diffractive gratings in the first stack.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 2A is a side view of an eyeglass temple of the frame in an embodiment of the see-through, mixed reality display device embodied as eyeglasses providing support for hardware and software components.

FIG. 2B is a top view of an embodiment of an integrated eye tracking and display optical system of a see-through, near-eye, mixed reality device.

FIG. 4A illustrates a side view of a portion of an eye tracking system including a waveguide according to an embodiment.

FIG. 4E illustrates an exemplary front view of a waveguide that includes an input-coupler and an output-coupler.

FIG. 4F illustrates how an eye motion box can be split into two zones by positioning two electronically switchable diffractive gratings (or two stacks of electronically switchable diffractive gratings) of the input-coupler horizontally adjacent to one another.

FIG. 4G illustrates how an eye motion box can be split into two zones by positioning two electronically switchable diffractive gratings (or two stacks of electronically switchable diffractive gratings) of the input-coupler vertically adjacent to one another FIG. 4H illustrates how an eye motion box can be split into four zones by positioning four electronically switchable diffractive gratings (or four stacks of electronically switchable diffractive gratings) of the input-coupler in a two-by-two tiled arrangement.

DETAILED DESCRIPTION

Certain embodiments of the present technology relate to waveguides that enable imaging of an eye, for the purpose of eye tracking, to be implemented without impairing the see-through properties of a mixed reality display device system. Additionally, such embodiments can advantageously be used with prescription eyewear. Further, such embodiments can be used to perform imaging of the eye that covers the entire eye movement range plus an inter-pupillary distance range and an eye relief distance range. However, before discussing such embodiments in additional detail, it is first useful to describe an exemplary see-through, mixed reality display device system with which embodiments of the present technology can be used.

Figure 1:
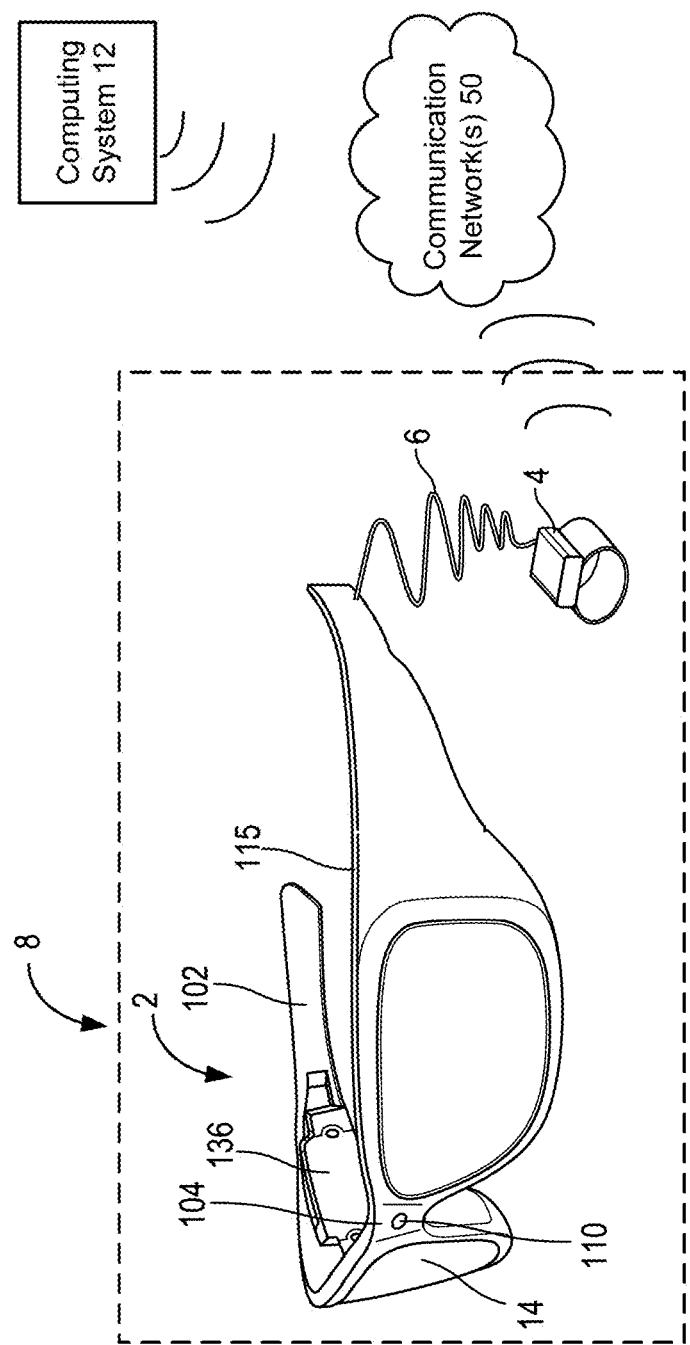
FIG. 1 is a block diagram depicting example components of one embodiment of a see-through, mixed reality display device system.

FIG. 1 is a block diagram depicting example components of one embodiment of a see-through, mixed reality display device system. System 8 includes a see-through display device as a near-eye, head mounted display device 2 in communication with processing unit 4 via wire 6. In other embodiments, head mounted display device 2 communicates with processing unit 4 via wireless communication. Processing unit 4 may take various embodiments. For example, processing unit 4 may be embodied in a mobile device like a smart phone, tablet or laptop computer. In some embodiments, processing unit 4 is a separate unit which may be worn on the user's body, e.g. the wrist in the illustrated example or in a pocket, and includes much of the computing power used to operate near-eye display device 2. Processing unit 4 may communicate wirelessly (e.g., WiFi, Bluetooth, infrared, RFID transmission, wireless Universal Serial Bus (WUSB), cellular, 3G, 4G or other wireless communication means) over a communication network 50 to one or more hub computing systems 12 whether located nearby in this example or at a remote location. In other embodiments, the functionality of the processing unit 4 may be integrated in software and hardware components of the display device 2.

Head mounted display device 2, which in one embodiment is in the shape of eyeglasses in a frame 115, is worn on the head of a user so that the user can see through a display, embodied in this example as a display optical system 14 for each eye, and thereby have an actual direct view of the space in front of the user.

The use of the term "actual direct view" refers to the ability to see real world objects directly with the human eye, rather than seeing created image representations of the objects. For example, looking through glass at a room allows a user to have an actual direct view of the room, while viewing a video of a room on a television is not an actual direct view of the room. Based on the context of executing software, for example, a gaming application, the system can project images of virtual objects, sometimes referred to as virtual images, on the display that are viewable by the person wearing the see-through display device while that person is also viewing real world objects through the display.

Frame 115 provides a support for holding elements of the system in place as well as a conduit for electrical connections. In this embodiment, frame 115 provides a convenient eyeglass frame as support for the elements of the system discussed further below. In other embodiments, other support structures can be used. An example of such a structure is a visor or goggles. The frame 115 includes a temple or side arm for resting on each of a user's ears. Temple 102 is representative of an embodiment of the right temple and includes control circuitry 136 for the display device 2. Nose bridge 104 of the frame 115 includes a microphone 110 for recording sounds and transmitting audio data to processing unit 4.

FIG. 2A is a side view of an eyeglass temple 102 of the frame 115 in an embodiment of the see-through, mixed reality display device embodied as eyeglasses providing support for hardware and software components. At the front of frame 115 is physical environment facing or outward facing video camera 113 that can capture video and still images which are transmitted to the processing unit 4.

The data from the camera may be sent to a processor 210 of the control circuitry 136, or the processing unit 4 or both, which may process them but which the unit 4 may also send to one or more computer systems 12 over a network 50 for processing. The processing identifies and maps the user's real world field of view.

Control circuits 136 provide various electronics that support the other components of head mounted display device 2. More details of control circuits 136 are provided below with respect to FIG. 3A. Inside, or mounted to the temple 102, are ear phones 130, inertial sensors 132, GPS transceiver 144 and temperature sensor 138. In one embodiment, inertial sensors 132 include a three axis magnetometer 132A, three axis gyro 132B and three axis accelerometer 132C (See FIG. 3A). The inertial sensors are for sensing position, orientation, and sudden accelerations of head mounted display device 2. From these movements, head position may also be determined.

Mounted to or inside the temple 102 is an image source or image generation unit 120. In one embodiment, the image source includes micro display 120 for projecting images of one or more virtual objects and lens system 122 for directing images from micro display 120 into a see-through waveguide 112. Lens system 122 may include one or more lenses. In one embodiment, lens system 122 includes one or more collimating lenses. In the illustrated example, a reflecting element 124 receives the images directed by the lens system 122 and optically couples the image data into the waveguide 112.

There are different image generation technologies that can be used to implement micro display 120. For example, micro display 120 can be implemented using a transmissive projection technology where the light source is modulated by optically active material, backlit with white light. These technologies are usually implemented using LCD type displays with powerful backlights and high optical energy densities. Micro display 120 can also be implemented using a reflective technology for which external light is reflected and modulated by an optically active material. Digital light processing (DLP), liquid crystal on silicon (LCOS) and Mirasol® display technology from Qualcomm, Inc. are all examples of reflective technologies. Additionally, micro display 120 can be implemented using an emissive technology where light is generated by the display, see for example, a PicoP™ display engine from Microvision, Inc. Another example of emissive display technology is a micro organic light emitting diode (OLED) display. Companies eMagin and Microoled provide examples of micro OLED displays.

FIG. 2B is a top view of an embodiment of a display optical system 14 of a see-through, near-eye, augmented or mixed reality device. A portion of the frame 115 of the near-eye display device 2 will surround a display optical system 14 for providing support for one or more optical elements as illustrated here and in the following figures and for making electrical connections. In order to show the components of the display optical system 14, in this case 14r for the right eye system, in the head mounted display device 2, a portion of the frame 115 surrounding the display optical system is not depicted.

In one embodiment, the display optical system 14 includes a waveguide 112, an optional opacity filter 114, see-through lens 116 and see-through lens 118. In one embodiment, opacity filter 114 is behind and aligned with see-through lens 116, waveguide 112 is behind and aligned with opacity filter 114, and see-through lens 118 is behind and aligned with waveguide 112. See-through lenses 116 and 118 may be standard lenses used in eye glasses and can be made to any prescription (including no prescription). In some embodiments, head mounted display device 2 will include only one see-through lens or no see-through lenses. Opacity filter 114, which is aligned with waveguide 112, selectively blocks natural light, either uniformly or on a per-pixel basis, from passing through waveguide 112. For example, the opacity filter enhances the contrast of the virtual imagery.

The waveguide 112 transmits visible light from micro display 120 to the eye 140 of the user wearing head mounted display device 2. The see-through waveguide 112 also allows visible light from in front of the head mounted display device 2 to be transmitted through itself 112 to eye 140, as depicted by arrow 142 representing an optical axis of the display optical system 14r, thereby allowing the user to have an actual direct view of the space in front of head mounted display device 2 in addition to receiving a virtual image from the micro display 120. Thus, the walls of waveguide 112 are see-through waveguide 112 includes a first reflecting surface (e.g., a mirror or other surface) or a first diffractive grating 124. Visible light from micro display 120 passes through lens 122 and becomes incident on reflecting surface or diffractive grating 124. The reflecting surface or the diffractive grating 124 reflects or diffracts the incident visible light from the micro display 120 such that visible light is trapped inside a substrate comprising waveguide 112 by internal reflection as described further below.

Infrared illumination and reflections also traverse the waveguide 112 for an eye tracking system 134 for tracking the position and gaze direction of the user's eyes. A user's eyes will be directed at a subset of the environment which is the user's area of focus or gaze. The eye tracking system 134 comprises an eye tracking illumination source 134A, which in this example is mounted to or inside the temple 102, and an eye tracking IR sensor 134B, which is this example is mounted to or inside a brow 103 of the frame 115. The eye tracking IR sensor 134B can alternatively be positioned between lens 118 and the temple 102. It is also possible that both the eye tracking illumination source 134A and the eye tracking IR sensor 134B are mounted to or inside the brow 103 of the frame 115.

The technology allows flexibility in the placement of entry and exit optical couplings (which can also be referred to as input- and output-couplers) to and from the waveguide's optical path for the image generation unit 120, the illumination source 134A and the eye tracking IR sensor 134B. The visible illumination representing images and the infrared illumination may enter from any direction about the waveguide 112, and one or more wavelength selective filters (e.g. 127) direct the illumination out of the waveguide centered about the optical axis 142 of the display optical system 14.

In one embodiment, the eye tracking illumination source 134A may include one or more infrared (IR) emitters such as an infrared light emitting diode (LED) or a laser (e.g. VCSEL) emitting about a predetermined IR wavelength or a range of wavelengths. In some embodiments, the eye tracking IR sensor 134B may be an IR camera or an IR position sensitive detector (PSD) for tracking glint positions.

In an embodiment, a wavelength selective filter 123 passes through visible spectrum light from the micro display 120 via reflecting surface 124 and directs the infrared wavelength illumination from the eye tracking illumination source 134A into the waveguide 112 where the IR illumination is internally reflected within the waveguide until reaching another wavelength selective filter 127 aligned with the optical axis 142.

From the IR reflections, the position of the pupil within the eye socket can be identified by known imaging techniques when the eye tracking IR sensor 134B is an IR camera, and by glint position data when the eye tracking IR sensor 134B is a type of position sensitive detector (PSD). The use of other types of eye tracking IR sensors and other techniques for eye tracking are also possible and within the scope of an embodiment.

After coupling into the waveguide 112, the visible illumination representing the image data from the micro display 120 and the IR illumination are internally reflected within the waveguide 112. In the example of FIG. 2B, after several reflections off the surfaces of the substrate, the trapped visible light waves reach an array of wavelength selective filters embodied in this example as selectively reflecting surfaces $126_1$ to $126_N$. Additionally, a wavelength selective filter 127 aligned with the optical axis of the display optical system is also positioned in the waveguide 112. Reflecting surfaces 126 couple visible light wavelengths incident upon those reflecting surfaces out of the substrate directed in the direction of the eye 140 of the user.

The reflecting surfaces 126 also pass infrared radiation within the waveguide. However, aligned with the optical axis 142 of the display optical system 14r, is one or more wavelength selective filters 127 which direct not only visible illumination but received infrared illumination from the illumination source 134A. For example, if the reflecting elements 126$_1$ to 126$_N$ are each reflecting different portions of the visible spectrum, the one or more wavelength selective filters 127 may reflect wavelengths in the red visible spectrum and the infrared spectrum. In other embodiments, the filters 127 can reflect wavelengths covering the entire visible spectrum or a larger portion thereof and the infrared spectrum for wavelengths of IR reflections and those generated by the IR illumination source.

Additionally, as will be discussed in more detail below with reference FIGS. 4A-4H an input-coupler (not specifically shown in FIGS. 2A and 2B, but shown in FIGS. 4A-4H) directs infrared reflections from the eye which pass through the see-through walls of the waveguide centered about the optical axis 142 into an optical path of the waveguide in a direction towards an output-coupler (not specifically shown in FIGS. 2A and 2B, but shown in FIGS. 4A and 4E-4H) that directs infrared light towards the eye tracking IR sensor 134B. Additionally, visible and infrared filters may be stacked in the direction from lens 116 to 118 so that they are all co-axial with the optical axis. For example, a bidirectional hot mirror placed in front of a visible reflecting element with respect to the eye lets visible light pass but reflects IR wavelengths. Additionally, the one or more filters 127 may be embodied as an active grating which is modulated between filtering wavelengths in the visible and infrared spectrums. This would be done at a rate fast enough for the human eye not to detect.

In an embodiment, each eye will have its own waveguide 112. When the head mounted display device has two waveguides, each eye can have its own micro display 120 that can display the same image in both eyes or different images in the two eyes. Further, when the head mounted display device has two waveguides, each eye can have its own eye tracking illumination source 134A and its own eye tracking IR sensor 134B. In another embodiment, there can be one waveguide with two optical axes, one for each eye, which spans the nose bridge and reflects visible and infrared light into both eyes.

In the embodiments described above, the specific number of lenses shown are just examples. Other numbers and configurations of lenses operating on the same principles may be used. Additionally, FIGS. 2A and 2B only show half of the head mounted display device 2. A full head mounted display device would include, for example, another set of see through lenses 116 and 118, another opacity filter 114, another waveguide 112 with one or more wavelength selective filters 127, another micro display 120, another lens system 122 physical environment facing camera 113 (also referred to as outward facing or front facing camera 113), eye tracking assembly 134, earphone 130, filter 123 and temperature sensor 138. Additional details of an exemplary head mounted display 2 are provided in United States Patent Application Publication No. 2012/0092328, entitled "Fusing Virtual Content Into Real Content," filed Oct. 15, 2010, by Flaks et al.

Figure 3A:
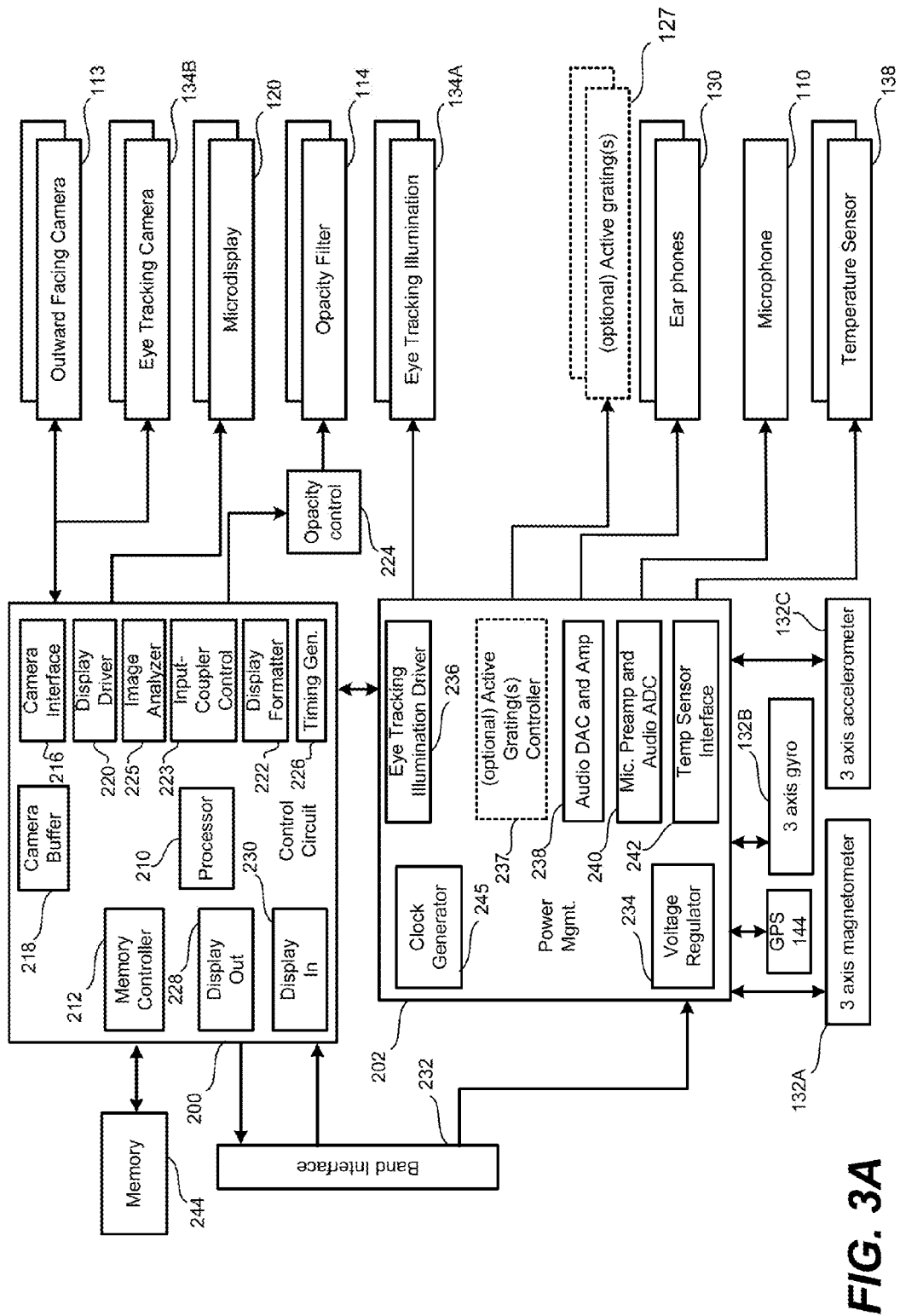
FIG. 3A is a block diagram of one embodiment of hardware and software components of a see-through, near-eye, mixed reality display device as may be used with one or more embodiments.
Figure 3B:
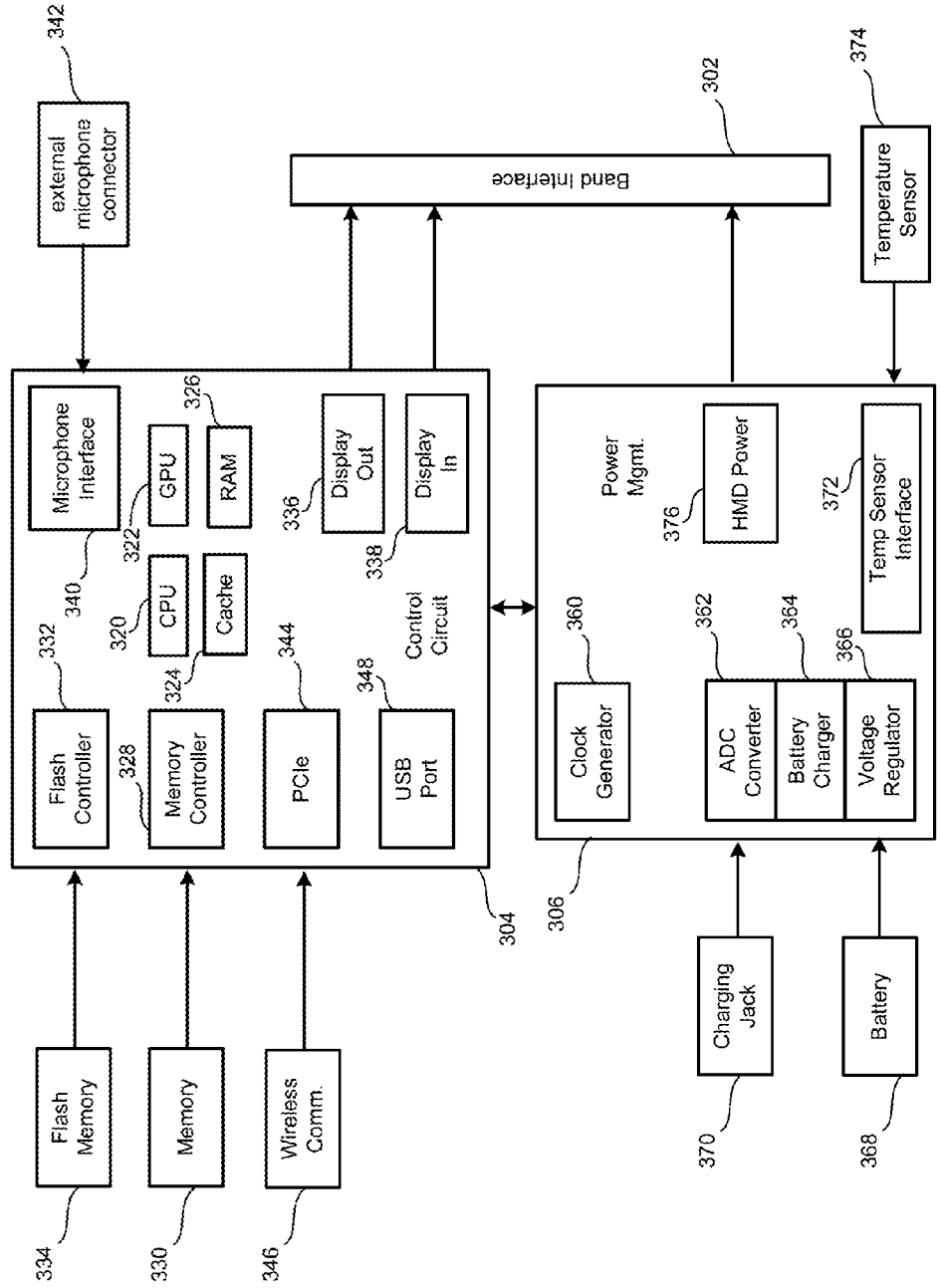
FIG. 3B is a block diagram describing the various components of a processing unit.

FIG. 3A is a block diagram of one embodiment of hardware and software components of a see-through, near-eye, mixed reality display device 2 as may be used with one or more embodiments. FIG. 3B is a block diagram describing the various components of a processing unit 4. In this embodiment, near-eye display device 2, receives instructions about a virtual image from processing unit 4 and provides data from sensors back to processing unit 4. Software and hardware components which may be embodied in a processing unit 4, for example as depicted in FIG. 3B, receive the sensory data from the display device 2 and may also receive sensory information from a computing system 12 over a network 50. Based on that information, processing unit 4 will determine where and when to provide a virtual image to the user and send instructions accordingly to the control circuitry 136 of the display device 2.

Note that some of the components of FIG. 3A (e.g., outward or physical environment facing camera 113, eye camera 134, micro display 120, opacity filter 114, eye tracking illumination unit 134A, earphones 130, one or more wavelength selective filters 127, and temperature sensor 138) are shown in shadow to indicate that there can be at least two of each of those devices, at least one for the left side and at least one for the right side of head mounted display device 2. FIG. 3A shows the control circuit 200 in communication with the power management circuit 202. Control circuit 200 includes processor 210, memory controller 212 in communication with memory 244 (e.g., D-RAM), a camera interface 216, a camera buffer 218, a display driver 220, a display formatter 222, an input-coupler controller 223, an image analyzer 225, a timing generator 226, a display out interface 228, and a display in interface 230. In one embodiment, all of components of control circuit 200 are in communication with each other via dedicated lines of one or more buses. In another embodiment, each of the components of control circuit 200 is in communication with processor 210.

Camera interface 216 provides an interface to the two physical environment facing cameras 113 and, in this embodiment, an IR camera as sensor 134B and stores respective images received from the cameras 113, 134B in camera buffer 218. Display driver 220 will drive microdisplay 120. Display formatter 222 may provide information, about the virtual image being displayed on microdisplay 120 to one or more processors of one or more computer systems, e.g. 4 and 12 performing processing for the mixed reality system. The display formatter 222 can identify to the opacity control unit 224 transmissivity settings with respect to the display optical system 14. Timing generator 226 is used to provide timing data for the system. Display out interface 228 includes a buffer for providing images from physical environment facing cameras 113 and the eye cameras 134B to the processing unit 4. Display in interface 230 includes a buffer for receiving images such as a virtual image to be displayed on microdisplay 120. Display out 228 and display in 230 communicate with band interface 232 which is an interface to processing unit 4.

The input-coupler controller 223 controls when each of a plurality of electronically switchable diffractive gratings is turned on, such that only one of the electronically switchable diffractive gratings is turned on at a time, as will be described in additional detail below. The image analyzer 225 analyzes two or more images of an eye, obtained using the IR eye tracking camera 134B, to determine which one of the electronically switchable diffractive gratings, when switched on, provides a best focused image of an eye (or a portion thereof), as will be described in additional details below. Additionally, or alternatively, the image analyzer can determine which one or more of a plurality of electronically switchable diffractive gratings includes an eye within its field-of-view.

Power management circuit 202 includes voltage regulator 234, eye tracking illumination driver 236, audio DAC and amplifier 238, microphone preamplifier and audio ADC 240, temperature sensor interface 242, active filter controller 237, and clock generator 245. Voltage regulator 234 receives power from processing unit 4 via band interface 232 and provides that power to the other components of head mounted display device 2. Illumination driver 236 controls, for example via a drive current or voltage, the eye tracking illumination unit 134A to operate about a predetermined wavelength or within a wavelength range. Audio DAC and amplifier 238 provides audio data to earphones 130. Microphone preamplifier and audio ADC 240 provides an interface for microphone 110. Temperature sensor interface 242 is an interface for temperature sensor 138. Active filter controller 237 receives data indicating one or more wavelengths for which each wavelength selective filter 127 is to act as a selective wavelength filter. Power management unit 202 also provides power and receives data back from three axis magnetometer 132A, three axis gyroscope 132B and three axis accelerometer 132C. Power management unit 202 also provides power and receives data back from and sends data to GPS transceiver 144.

FIG. 3B is a block diagram of one embodiment of the hardware and software components of a processing unit 4 associated with a see-through, near-eye, mixed reality display unit. FIG. 3B shows controls circuit 304 in communication with power management circuit 306. Control circuit 304 includes a central processing unit (CPU) 320, graphics processing unit (GPU) 322, cache 324, RAM 326, memory control 328 in communication with memory 330 (e.g., D-RAM), flash memory controller 332 in communication with flash memory 334 (or other type of non-volatile storage), display out buffer 336 in communication with see-through, near-eye display device 2 via band interface 302 and band interface 232, display in buffer 338 in communication with near-eye display device 2 via band interface 302 and band interface 232, microphone interface 340 in communication with an external microphone connector 342 for connecting to a microphone, PCI express interface for connecting to a wireless communication device 346, and USB port(s) 348.

In one embodiment, wireless communication component 346 can include a Wi-Fi enabled communication device, Bluetooth communication device, infrared communication device, cellular, 3G, 4G communication devices, wireless USB (WUSB) communication device, RFID communication device etc. The wireless communication component 346 thus allows peer-to-peer data transfers with for example, another display device system 8, as well as connection to a larger network via a wireless router or cell tower. The USB port can be used to dock the processing unit 4 to another display device system 8. Additionally, the processing unit 4 can dock to another computing system 12 in order to load data or software onto processing unit 4 as well as charge the processing unit 4. In one embodiment, CPU 320 and GPU 322 are the main workhorses for determining where, when and how to insert virtual images into the view of the user.

Power management circuit 306 includes clock generator 360, analog to digital converter 362, battery charger 364, voltage regulator 366, see-through, near-eye display power source 376, and temperature sensor interface 372 in communication with temperature sensor 374 (located on the wrist band of processing unit 4). An alternating current to direct current converter 362 is connected to a charging jack 370 for receiving an AC supply and creating a DC supply for the system. Voltage regulator 366 is in communication with battery 368 for supplying power to the system. Battery charger 364 is used to charge battery 368 (via voltage regulator 366) upon receiving power from charging jack 370. Device power interface 376 provides power to the display device 2.

Waveguide Eye Tracking System

FIGS. 4A-4H will now be used to describe specific features of a waveguide 412, according to various embodiment of the present technology. Initially, FIGS. 4A and 4B will be used to describe portions of the waveguide 412 that are used to collect infrared light reflected from an eye 440 and provide the infrared light to an eye tracking IR sensor (e.g., 134B discussed above with reference to FIGS. 2B and 3A) for use in eye tracking. Accordingly, the waveguide 412 can also be referred to as an eye tracker waveguide 412 or an eye tracking waveguide 412. More generally, the waveguide can be referred to as an apparatus for use in tracking an eye.

The waveguide 412 can be incorporated into a see-through mixed reality display device system, such as the one described above with reference to FIGS. 1-3B, but is not limited to user therewith. For example, the waveguide 412 can be used to implement the waveguide 112 (or a portion thereof) discussed above with reference to FIGS. 1, 2A and 2B. Alternatively, the waveguide 412 can be located adjacent to the waveguide 112 or used in place of the waveguide 112, depending upon implementation. A separate instance of the waveguide 412 can be provided for each of the left and right eyes of a user whose eyes are being tracked. If used in the see-through mixed reality display device system described above with reference to FIGS. 1-3B, the waveguide 412 may be positioned next to or between see-through lenses (e.g., 116 and/or 118), which may be standard lenses used in eye glasses and can be made to any prescription (including no prescription). The waveguide 412 can alternatively be used with any system that is intended to perform eye tracking based on infrared light reflected from an eye.

FIG. 4A illustrates a side view of a portion of an eye tracking system 400 including the waveguide 412, and thus, the portion of the eye tracking system shown in FIG. 4A can be referred to as a waveguide eye tracker 400. The waveguide 412 includes an input-coupler 414 and an output-coupler 424. Also shown in FIG. 4A is a lens module 430, including one or more lenses, that is configured to convert the angular space of the rays within the waveguide 412 to two-dimensional (2D) space after the rays exit the waveguide 412 proximate the output-coupler 424. Explained another way, the lens module 430, which can also be referred to as the imaging lens 430, is used to convert angular encoded infrared light beams into two-dimensional (2D) spatially encoded infrared light beams. After being converted to two-dimensional space, the infrared light beams are incident on a two-dimensional plane of the eye tracking IR sensor 134B, as shown in FIG. 4A. The eye tracking IR sensor 134B produces eye tracking data in dependence on the two-dimensional spatially encoded infrared light beams that are incident on the sensor 134B.

More generally, the eye tracking IR sensor 134B produces an image of the eye 440 in dependence on infrared light beams that exit the waveguide 412 at the output-coupler 424. The infrared light beams that exit the waveguide 412 at the output-coupler 424 pass through the lens module 430 before being incident on the eye tracking IR sensor 134B. As just explained, the lens module 430 converts the infrared light beams that exit the waveguide 412 at the output-coupler 424 from angularly encoded infrared light beams to two-dimensional spatially encoded infrared light beams. Alternatively, the functionality of the lens module 430 can be completely or partially built into the output-coupler 424, potentially elimination the lens module 430.

In general, the input-coupler 414 of the waveguide is preferably axially aligned with an eye 440, such that when the eye 440 is illuminated with infrared light, infrared light beams reflected from the eye will be incident on the input-coupler 414 of the waveguide 412. More generally, infrared light will be reflected from the eye 440, e.g., when the eye 440 is illuminated by infrared light produced by the eye tracking illumination unit 134A, as explained above.

The output-coupler 424 is preferably located in close proximity to the sensor or camera (e.g., eye tracking IR sensor 134B) that is used to image the eye. As was mentioned above, such a sensor or camera can be mounted to or inside the brow (e.g., 103) of a frame (e.g., 115). Alternatively, a sensor or camera can be mounted to or inside the temple or side arm (e.g., 102) of a frame, in which case, the relative positions of the input-coupler 414 and the output-coupler 424 may be rotated by ninety degrees. As was explained above, a lens module (e.g., 430) can be located between the output-coupler 424 and the sensor (e.g., eye tracking IR sensor 134B). In accordance with an embodiment, the output coupler incorporates lens power that partially or totally replaces the lens module 430. For example, in one embodiment the output-coupler 424 provides wedge power and lens power in a single diffraction optical element.

In accordance with an embodiment, the horizontal-by-vertical area of the input-coupler is 28 mm×16 mm, which defines the eye tracking area. Alternative areas are also possible and within the scope of an embodiment. The aperture of the output-coupler can be, e.g., 3.7 mm, but smaller or larger apertures are also possible and within the scope of an embodiment. The f-number of the lens module 430 can be, e.g., 1.35, but smaller or larger f-numbers are also possible and within the scope of an embodiment. The thickness of the waveguide 412 is preferably 1 mm or less, but greater thicknesses are possible and within the scope of an embodiment. The waveguide 412 can be manufactured using BK7 optical glass, but the use of other optical materials are also possible and within the scope of an embodiment. Assuming the wavelength of the infrared light used for eye tracking is 850 nm, the waveguide 412 preferably provides for total internal reflections for an angle of incidence (AOI) greater than 42 degrees at 850 nm. It is also within the scope of an embodiment that alternative infrared wavelengths can be used. To achieve total internal reflections below the critical angle of the substrate, a reflective coating 422 can be applied to outer surfaces of the waveguide 412 at the air-glass interface. This coating is useful in embodiments where the range of internal angles generated by the input coupler is greater than what can be supported by the substrate. For example, if the eye tracking area is 28 mm×16 mm and the eye relief (distance from the eye to the input coupler) is around 20 mm, if the region of the input coupler nearest the imaging lens generates an internal angle just above the critical angle of BK7, then the internal angles generated by the region of the input coupler furthest away from the imaging lens would need to be above 90 degrees which is essentially impossible. Alternatively, if the input coupler was designed to generate internal angles of around 70 degrees for the region of the input coupler furthest away from the imaging lens then the internal angles generated by the region of the input coupler nearest the imaging lens would be less than the critical angle of BK7, thus requiring a coating to extend the internal reflection.

Figure 4B:
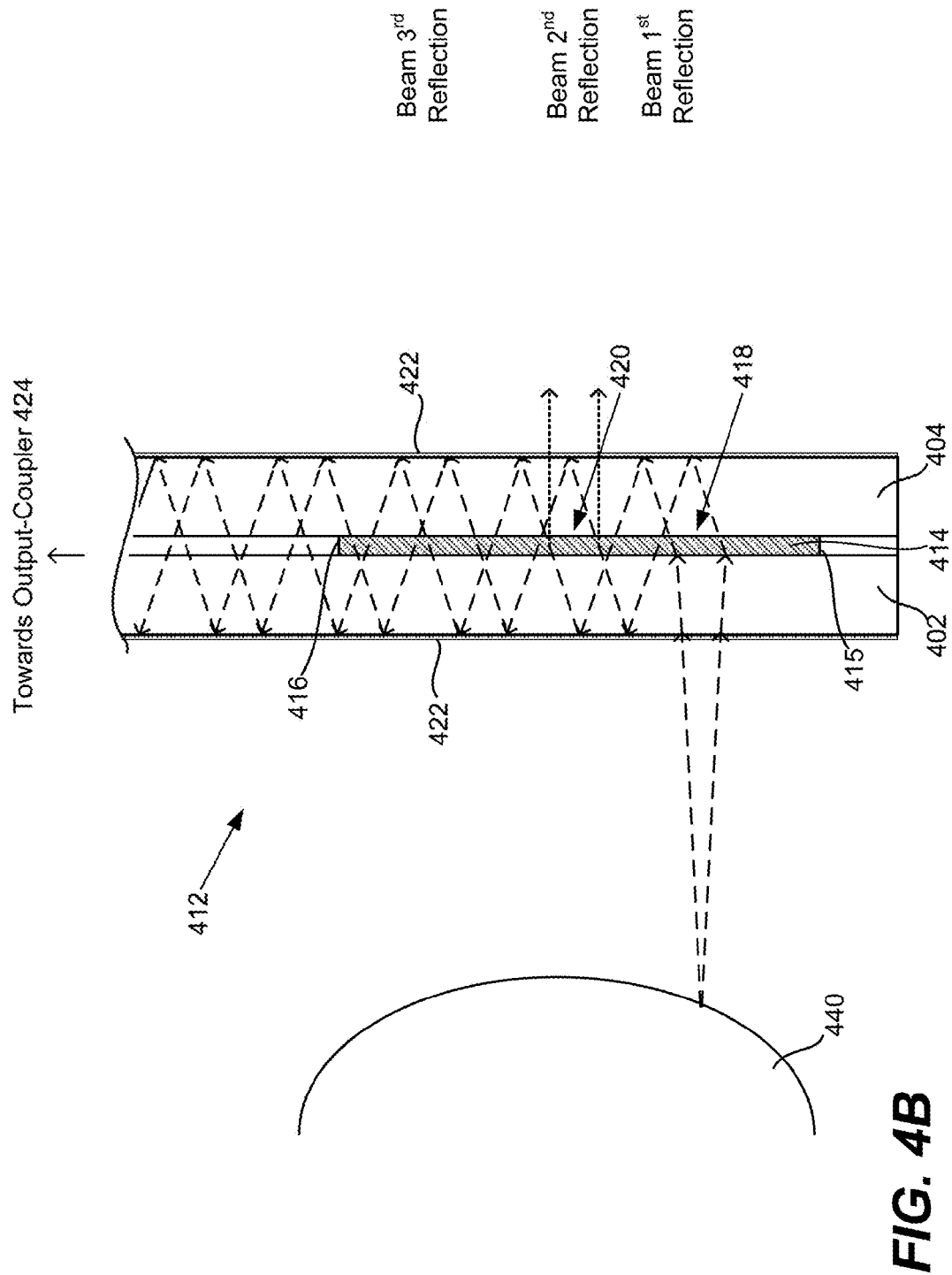
FIG. 4B is a blow up of the portion of the waveguide introduced in FIG. 4A.

FIG. 4B, which is a blow up of the portion of the waveguide 412 that includes the input-coupler 414, will now be used to describe additional details of the waveguide 412, according to an embodiment. Referring to FIG. 4B, the waveguide 412 is shown as including a first transparent layer 402, a second transparent layer 404, and the input-coupler 414. Although not specifically shown in FIG. 4B, the output-coupler 424 can be similarly between the first and second transparent layers 402, 404. The transparent layers 402, 404 can be made of glass or optical plastic, but are not limited thereto. It is noted that even if the transparent layers 402, 404 are made of optical plastic, the interface between such layers and air will still be referred to as an air-glass interface. As shown in FIG. 4B, the input-coupler 414 has a lower boundary 415 and an upper boundary 416, with the upper boundary 416 being closer to the output-coupler 424 than the lower boundary 415.

The input-coupler 414, which is a diffractive element, is configured to have an angle of diffraction that is different than the angle of incidence. More specifically, the diffractive element input-coupler 414 adjusts the angle of light passing through the first transparent layer 402 so that the angle of the light as it meets the air-glass interface of the transparent layer 404 is beyond the critical angle and thus reflects internally in the waveguide 412. The light will then pass out of the waveguide 412 at the output-coupler 424, as mentioned above.

When the input-coupler 414 is positioned in front of an eye 440 that is illuminated with infrared light, infrared light beams (one example of which is shown by dashed arrows in FIG. 4B) reflected from the eye 440 pass through the first transparent layer 402 and are incident on the input-coupler 414. These infrared light beams enter the waveguide 412 at the input-coupler 414, propagate within the waveguide 412 from the input-coupler 414 to the output-coupler 424 by way of total internal reflections, and exit the waveguide 412 proximate the output-coupler 424. Explained another way, infrared light reflected from the eye 440 is imaged by the input-coupler 414 and simultaneously diffracted into waveguide mode by diffracting the infrared light so that the diffracted infrared light is incident on surfaces of the waveguide 412 at a greater angle than the critical angle for total internal reflection.

The input-coupler 414 can be implemented as a diffraction-grating, examples of which are discussed below. The output-coupler 424, which can be reflective, diffractive or refractive, or a combination thereof, can be implemented, e.g., as a linear grating type of output-coupler, a holographic grating type of output-coupler, a prism or another optical coupler capable of causing infrared light to exit the waveguide 412. The output-coupler 424 can additionally have lens power integrated in the prescription which could replace some or all of the lens power of the lens module 430. In one such embodiment, the output-coupler 424 can be a volume Bragg Grating with wedge and lens power. The lens power of the output-coupler 424 could provide some or all of the lens power of the lens module 430. In one embodiment, the output-coupler 424 provides a small correction to the lens module 430, for example by providing aspheric correction. Referring briefly back to FIG. 4A, the purpose of the output-coupler 424 is to cause infrared light to exit the waveguide 412 toward the lens module 430 and/or towards the eye tracking IR sensor 134B. The infrared light is then finally imaged by the lens module 430 (or the output-coupler 424 itself) onto the eye tracking IR sensor 134B. The eye tracking IR sensor can be, e.g., a charge-coupled device (CCD) or CMOS two-dimensional (2D) pixel sensor array, but is not limited thereto.

In an embodiment, the input-coupler 414 and the output-coupler 424 are positioned relative to one another to achieve telecentricity. Under this circumstance, the entrance pupil is located at infinity, which makes the input-coupler object-space telecentric. This can advantageously provide an orthographic projection of the eye 440. Telecentricity can also be achieved by designing the angular bandwidth of the input-coupler 414 so that it centers on light which is parallel for all light from the eye plane. This does not necessarily mean that the angular bandwidth centers on light which is orthogonal to the waveguide. For example, it may be advantageous to view the eye plane from a direction below the eye plane (looking up at the eye) to reduce obscuration due to eye lashes. Explained another way, to achieve telecentricity in object space the angular bandwidth of each point of the input-coupler 414 should be centered on a chief ray where all chief rays of the input-coupler 414 are substantially parallel.

In accordance with an embodiment, the input-coupler 414 has a lens power and a wedge power. The lens power of the input-coupler 414 preferably has a focal length that is equal to a distance between the eye 440 and the input-coupler 414, which advantageously causes infrared light (reflected from the eye 440, and incident on the input-coupler 414) to be collimated within the waveguide 412. For example, if the distance between the eye 440 and the input-coupler 414 is 20 millimeters (mm), then the focal length of the lens power of the input-grating is preferably 20 mm. The wedge power, which can also be referred to as wedge diffractive power or prismatic power, diffracts the infrared light (which is preferably collimated) into waveguide mode. The wedge power is preferably selected so that the infrared light incident on a portion of input-coupler 414 near its upper boundary 416 is diffracted internally so that the angle of incidence to the air-glass interface of the waveguide is greater than the total internal reflection (TIR) angle of the waveguide 412 (and therefore guided by the waveguide 412). In addition the wedge power is preferably selected so that infrared light incident on a portion of the input-coupler 414 near its lower boundary 415 is diffracted internally so that the angle of incidence to the air-glass interface of the waveguide is not too large (e.g., no greater than 70 degrees) to avoid rays travelling almost parallel to surfaces of the waveguide 412. In accordance with an embodiment, the lens power and the wedge power are combined mathematically and implemented by a single grating prescription. This can be achieved by mathematically fitting a phase polynomial that satisfies the conditions of input angles to output angles across a surface of the grating. The generating of a phase polynomial of this type can be used to program an electron beam etching machine to produce a surface grating in a medium, such as chrome or glass. This in turn can be used to generate a phase copy master hologram, which in turn can be used in a contact copy process to mass produce the diffractive grating type of input-coupler 414.

Beams reflected within the waveguide 412 are close together, with the distance between such beams being dependent on an angle of propagation within the waveguide 412, the thickness of the waveguide 412, and the beam width. Since there is a desire to make the thickness of the waveguide 412 as thin as practical, different beams within the waveguide 412 may be very close to one another and potentially overlap one another.

The eye tracker optical system as a whole acts like a relay lens system that reimages light from an eye plane (e.g., associated with the eye 440) to a camera sensor plane (e.g., associated with the eye tracking IR sensor 134B). In an embodiment, the magnification of the total system is much less than one (a de-magnification) since the eye tracking IR sensor 134B (which can also be referred to as a camera sensor or image sensor) is much smaller than the object plane (the eye plane). The input-coupler 414 preferably causes different beams of infrared light that are incident on different horizontal and vertical positions of the input-coupler 414 to propagate within the waveguide 412 at respective different angles of reflection, and exit the output-coupler 424 at respective different angles of incidence relative to the surface of the waveguide 412 through with the infrared light beams exit. Explained another way, the input-coupler 414 preferably cause angular encoding of the infrared light beams that are incident on the input-coupler 414, thereby enabling the infrared light beams that exit the waveguide 412 through the output-coupler 424 to be imaged (e.g., by the eye tracking IR sensor 134B) in a manner that distinguishes between infrared light beams that were incident on different horizontal and vertical positions of the input-coupler 414.

As mentioned above, the lens power of the input-coupler 414 preferably has a focal length that is equal to a distance between the eye 440 and the input-coupler 414, which advantageously causes infrared light (reflected from the eye 440, and incident on the input-coupler 414) to be collimated within the waveguide. While this is a preferred condition, such a condition is not easy to consistently achieve since different people have differently shaped noses and other facial features and different eye locations. Additionally, each time the same person puts on an HMD device that includes the waveguide 412 and/or adjusts the HMD device, the distance between the person's eye and the input-coupler 414 may change. It is noted that the distance between the eye 440 and the input-coupler 414 can also be referred to as the eye relief distance.

When the focal length of the lens power of the input-coupler 414 is not equal to the distance between the input-coupler 414 and the eye 440 (i.e., not equal to the eye relief distance), then infrared light beams traveling within the waveguide 412 by way of total internal reflections will not be perfectly collimated. A problem with this condition is that two or more light beams reflected into the waveguide (through the input-coupler 414) from the same point on the eye 440, after traveling from the input-coupler 414 to the output-coupler 424 by way of total internal reflections, will exit the waveguide (through the output-coupler 424) at two or more different locations thereby resulting in multiple (e.g., double, triple, etc.) images being generated by lens module 430 and the eye tracking IR sensor 134B. In other words, two or more beams coming from the same point in the eye plane will be convergent or divergent within the waveguide 412 such that two or more separate images are formed by the eye tracking IR sensor 134B. Such multiple (e.g., double, triple, etc.) imaging is undesirable because it reduces the accuracy of the eye tracking and/or makes it much more complex to perform eye tracking.

Figure 4C:
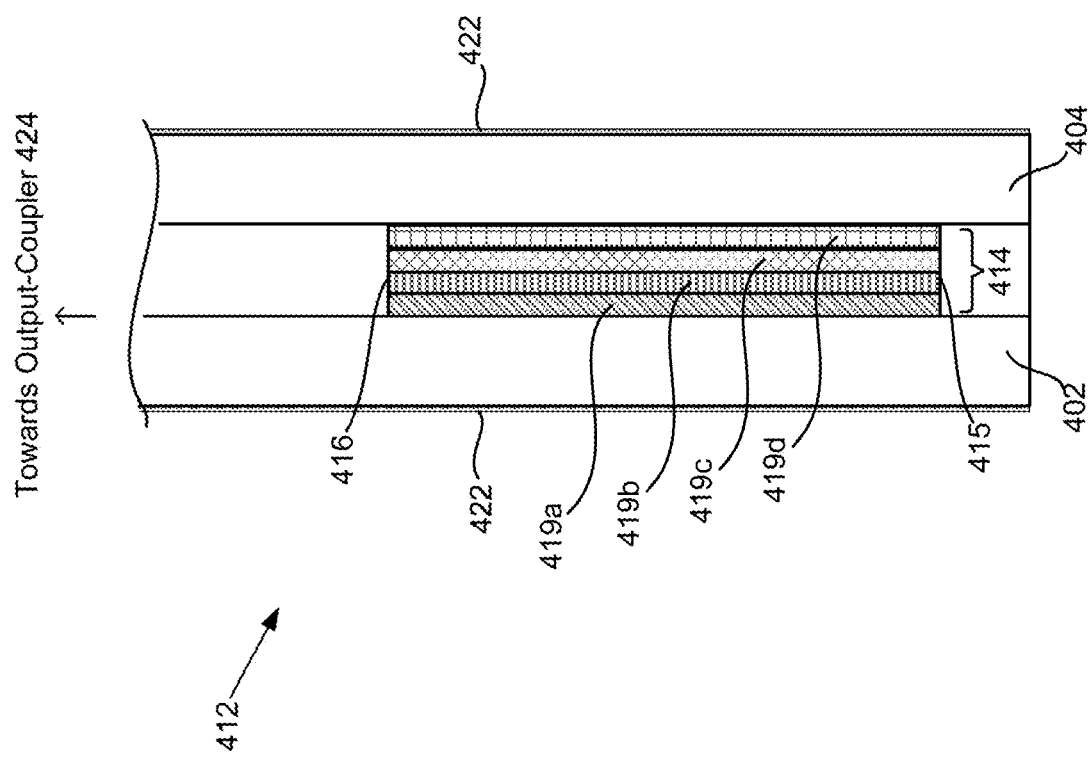
FIG. 4C is a blow up of the portion of the waveguide introduced in FIG. 4A, according to an embodiment where the input-coupler includes a stack of two or more electronically switchable diffractive gratings arranged parallel to one another.

In accordance with certain embodiments, rather than including a single diffraction grating that has a single lens power, and thus a single focal length, the input-coupler 414 includes a stack of two or more electronically switchable diffractive gratings arranged parallel to one another, as shown in FIG. 4C. More specifically, referring to FIG. 4C, the input-coupler 414 is shown as including a stack of four electronically switchable diffractive gratings, labeled 419a, 419b, 419c, 419d, arranged parallel to one another. The electronically switchable diffractive gratings 419a, 419b, 419c, 419d can be referred to individually as an electronically switchable diffractive grating 419, or collectively as the electronically switchable diffractive gratings 419. Each of the electronically switchable diffractive gratings 419 has a respective lens power and a respective prismatic power. The lens power of each of the electronically switchable diffractive gratings 419 differ from one another such that each of the electronically switchable diffractive gratings has a different focal length. Such an embodiment enables a user's eye to be imaged using two or more different focal lengths, so that a best focused image can be selected for use in eye tracking. More specifically, such an embodiment enables two or more images of an eye, obtained using the eye tracking IR sensor 134B, to be analyzed to determine which one of the electronically switchable diffractive gratings 419, when switched on, provides a best focused image of an eye or portion thereof (e.g., a best focused image of the pupil of the eye).

For an example, assume that the potential eye relief distance range is from 7 mm to 27 mm, which spans 20 mm. If there are four electronically switchable diffractive gratings 419, as in FIG. 4C, then each of the electronically switchable diffractive gratings 419 can have a focal length that is centered about a different 5 mm span of the 20 mm eye relief distance range. Continuing with this example, the four different focal lengths for the four electronically switchable diffractive gratings 419 can be 9.5 mm, 14.5 mm, 19.5 mm and 24.5 mm. For a more specific example, the focal length for the electronically switchable diffractive grating 419a can be 9.5 mm, the focal length for the electronically switchable diffractive grating 419b can be 14.5 mm, the focal length for the electronically switchable diffractive grating 419c can be 19.5 mm, and the focal length for the electronically switchable diffractive grating 419c can be 24.5 mm. Alternatively, the order can be rearranged, as there is no requirement that the electronically switchable diffractive gratings 419 be in order from the shortest to longest focal length. The input-coupler 414 can alternatively include more or less than four stacked electronically switchable diffractive gratings 419. More generally, in the embodiment being described with reference to FIG. 4C, the input-coupler 414 includes a stack of two or more electronically switchable diffractive gratings 419 arranged parallel to one another, wherein each of the electronically switchable diffractive gratings 419 has a respective lens power and a respective prismatic power, and wherein the lens power of each of the electronically switchable diffractive gratings 419 differ from one another such that each of the electronically switchable diffractive gratings has a different focal length. The prismatic power can be the same for all of the plurality of electronically switchable diffractive gratings 419, but that need not be the case.

In accordance with an embodiment, each of the electronically switchable diffractive gratings is an electronically switchable Bragg grating (ESBG). In such an embodiment, the electronically switchable Bragg gratings will have a Bragg wavelength that is matched to the infrared wavelength of the infrared light that illuminates the eye being tracked. In accordance with another embodiment, each of the electronically switchable diffractive gratings is an electronically switchable lithium niobate diffraction grating. In still another embodiment, each of the electronically switchable diffractive gratings is an electronically switchable polymer liquid crystal polymer slices (POLYCRYPS) diffraction grating. The use of other types of electronically switchable diffractive gratings are also possible, and within the scope of the present technology.

The stack of electronically switchable diffractive gratings 419 is sandwiched between the first and second transparent layers 402, 404, which as mentioned above, can be made of glass or optical plastic, but are not limited thereto. In accordance with an embodiment, each of the electronically switchable diffractive gratings 419 includes its own pair of transparent layers (e.g., made of glass or optical plastic) between which is located a material (e.g., Holographic Polymer-Dispersed Liquid Crystals) whose refractive index can be switched between two different values. Such transparent layers can be coated with a transparent conductive film (TCF), e.g., made of a transparent conductive oxide (TCO), such as, but not limited to, tin-doped indium oxide (ITO), aluminum doped zinc-oxide (AZO) or indium-doped cadmium-oxide. For another example, the transparent conductive film that coats the pair of transparent layers of each electronically switchable diffractive gratings 419 can be made of a transparent conduct polymer, such as, but not limited to, poly(3,4-ethylenedioxythiophene) (PEDOT) or poly(4,4-dioctylcyclopentadi-thiophene). Such transparent conductive films are used to selectively apply a voltage potential difference between sides of the electronically switchable diffractive gratings 419 to selectively turn them on and off.

Each of the electronically switchable diffractive gratings 419 can be normally switched on, or normally switched off. If an electronically switchable diffractive grating 419 is normally switched on, that means when no voltage potential difference is applied between the two sides of the grating, the grating is turned on; and application of a voltage potential difference between the sides of the grating, turns the grating off. If an electronically switchable diffractive grating 419 is normally switched off, that means when no voltage potential difference is applied between the sides of the grating, the grating is turned off; and application of a voltage potential difference between the sides of the grating, turns the grating on. When an electronically switchable diffractive grating 419 is turned off, infrared light that is reflected from a user's eye and is incident on the grating passes through the grating essentially as if the grating was not there. More specifically, when an electronically switchable diffractive grating 419 is turned off its refractive index approximately matches that of the surrounding polymer of the waveguide so that the grating is essentially transparent to the infrared light incident thereon. When an electronically switchable diffractive grating 419 is turned on, infrared light that is reflected from a user's eye and is incident on the grating is coupled into the waveguide 412 and propagates within the waveguide 412 from the turned-on grating to the output-coupler 424 by way of total internal reflections, and exits the waveguide proximate the output-coupler 424.

In accordance with an embodiment, the input-coupler controller 223 (introduced in the discussion of FIG. 3A) controls the turning on and off of the electronically switchable diffractive gratings 419, such that only one of the electronically switchable diffractive gratings is turned on at a time. While each individual one of the electronically switchable diffractive gratings 419 is turned on, the IR eye tracking sensor 134B images the eye (i.e., produces an image of the eye) in dependence on infrared light beams that are reflected from a user's eye that enter the waveguide 412 at the turned on grating 419 of the input-coupler 414, propagate within the waveguide 412 by way of total internal reflections, and exit the waveguide 412 at the output-coupler 424. For example, referring to FIG. 4C, while the electronically switchable diffractive grating 419a is turned on (and the gratings 419b, 419c and 419d are turned off), the IR eye tracking sensor 134B images the eye (i.e., produces an image of the eye) in dependence on infrared light beams that are reflected from a user's eye that enter the waveguide 412 at the turned on grating 419a. Still referring to FIG. 4C, while the electronically switchable diffractive grating 419b is turned on (and the gratings 419a, 419c and 419d are turned off), the IR eye tracking sensor 134B images the eye in dependence on infrared light beams that are reflected from the user's eye that enter the waveguide 412 at the turned on grating 419b. While the electronically switchable diffractive grating 419c is turned on (and the gratings 419a, 419b and 419d are turned off), the eye tracking IR sensor 134B images the eye in dependence on infrared light beams that are reflected from the eye and enter the waveguide 412 at the turned on grating 419c. Finally, while the electronically switchable diffractive grating 419d is turned on (and the gratings 419a, 419b and 419c are turned off), the eye tracking IR sensor 134B images the eye in dependence on infrared light beams that are reflected from the eye that enter the waveguide 412 at the turned on grating 419d.

The image of the eye that is obtained using the one of the electronically switchable diffractive gratings 419 that has a focal length that is closest to the actual eye relief distance will be the most in-focus of the multiple images. In accordance with an embodiment, the image analyzer 225 (introduced in the discussion of FIG. 3A) analyzes multiple images of the eye, obtained using the eye tracking IR sensor, to determine which one of the electronically switchable diffractive gratings 419, when switched on, provides a best focused image of the eye or portion thereof (e.g., of the pupil of the eye). In accordance with specific embodiments, the image analyzer 225 can use one or more autofocus techniques, which are well known in the art, to determine which one of the plurality of electronically switchable diffractive gratings 419 (each having a different focal length) provides for the best focused image. Such autofocus techniques may, for example, determine measures of resolution, contrast, and/or entropy to determine a metric of image sharpness, or more generally, a metric of focus. For example, a metric of resolution can be determined and used as the metric of focus. Because image details blur as an image is defocused and resolution is lost, the higher the resolution the better the focus. In certain embodiments, a metric of resolution is the high-frequency content of a Fourier frequency spectrum. For another example, a metric of contrast can be determined and used as the metric of focus. An image is sharper when in focus than when not in focus, which results in a greater contrast between neighboring pixels of the image. In certain embodiments, the slope of a plot can be analyzed to determine a metric of contrast, wherein the steeper the slope the greater the contrast, and thus, the better the focus. These are just a few examples of autofocus techniques that can be used, which are not meant to be all encompassing. Such techniques can be implemented using circuitry and/or an algorithm performed using a processor (e.g., 210). In other words, an image analysis module can be implemented using hardware, firmware or software, or a combination thereof.

In accordance with an embodiment, once the electronically switchable diffractive grating 419 that provides for the most focused image is identified, the input-coupler controller 223 (introduced in the discussion of FIG. 3A) causes the one of the electronically switchable diffractive gratings 419, which provides the most focused image of the eye, to be used for imaging the eye during eye tracking. If each of the electronically switchable diffractive gratings 419 is normally turned off, then the input-coupler controller 223 will cause an appropriate voltage potential difference to be applied between the opposing sides of the grating 419 that provided for the most focused image of the eye, in order to turn that grating 419 on while eye tracking is being performed. If each of the electronically switchable diffractive gratings 419 is normally turned on, then the input-coupler controller 223 will cause an appropriate voltage potential difference to be applied between the opposing sides of the one or more of the gratings 419 that did not provide for the most focused image of the eye, in order to turn those gratings 419 off while eye tracking is being performed.

Certain embodiments of the present technology reduce and preferably minimize the effects of multiple images that are inherent in a waveguide eye tracker 400 when the distance between the eye 440 and the input-coupler 414 (i.e., the eye relief distance) is not exactly the same as the focal length of the input-coupler 414. Some such embodiments do this by reducing and preferably minimizing the distance(s) between the multiple images by designing the input-coupler 414 to have a very narrow angular bandwidth in the tangential direction (i.e., in the direction of propagation). More specifically, in accordance with an embodiment, the angular bandwidth (ABW) of the input-coupler 414 is no more than 5 degrees, preferably no more than 2 degrees, more preferably between 1 and 2 degrees, and even more preferably ~1.5 degrees.

As the term is used herein, the angular bandwidth (ABW) of a diffraction grating, such as the input-coupler 414, is the angular range around the peak diffraction efficiency (DE) of the incident angle within which the DE is greater than or equal to 50% of the peak DE. Accordingly, the ABW can more accurately be referred to herein as the full width half max (FWHM) ABW. Beneficially, a diffraction grating having such a narrow ABW can be readily designed and manufactured.

By limiting the ABW to such a narrow angle, the extent that infrared light reflected from the same point on the eye 440 may be non-collimated within the waveguide is significantly limited. In other words, the very narrow ABW of the input-coupler 414 limits how much infrared light beams that are reflected from the same point on the eye 440 (and enter the waveguide at the input-coupler 414) can deviate from being perfectly collimated within the waveguide 412. More generally, use of an input-coupler 414 having a narrow ABW limits the cone angle of reflected light from the eye and thereby increases the depth of field of imaging, thereby making the waveguide eye tracker 400 compatible with a range of distances between an eye and the input-coupler 414.

As is known in the art, a diffraction grating can be designed to have a periodic variation of the refractive index, so that a large diffraction efficiency may be reached in a wavelength range (bandwidth) around a certain wavelength. For example, where the diffraction grating is a volume Bragg grating, the diffracted wavelength, $\lambda B$ (which is also known as the Bragg wavelength), is defined by the Bragg condition, $\sin \theta_B = \lambda/(2 n_{eff} \Lambda)$, and is proportional to the waveguide's effective refractive index (neff) and the grating periodicity ($\Lambda$) for a fixed Bragg incident direction $\theta_B$. A volume Bragg grating includes grating planes (also referred to as fringes, fringe planes or Bragg planes) that define the grating periodicity ($\Lambda$). K-vectors of the volume Bragg grating are normal to (i.e., perpendicular to) these Bragg planes. In accordance with an embodiment, the Bragg wavelength, $\lambda B$, is matched to (i.e., substantially equal to) the wavelength of the infrared light that is used for eye tracking. More generally, K-vectors of a diffraction grating are normal to (i.e., perpendicular to) grating planes of the diffraction grating.

Referring briefly back FIG. 4B, when an infrared light beam (represented by dashed arrows) is diffracted at the region labeled 418 of the input-coupler 414, the infrared light beam is diffracted with high efficiency into waveguide mode. If the prescription of the input-coupler 414 is exactly the same at the region labeled 420, as it is at the region labeled 418, then a high percentage of the infrared light (represented by the dotted arrows) will be diffracted out of the waveguide at the region labeled 420. This is undesirable since it results in portions of the infrared light that is diffracted into the waveguide 412 (by the input-coupler 414) from not reaching the output-coupler 424, thereby significantly reducing the overall optical efficiency of the device and in image processing terms, reducing the signal-to-noise ratio (SNR).

In accordance with certain embodiments, to reduce and preferably minimize the amount of infrared light that is diffracted out of the waveguide by the input-coupler 414, the prescription of the input-coupler 414 is varied between the lower boundary 415 and upper boundary 416 of the input-coupler 414. This is accomplished by designing the each of the electronically switchable diffraction gratings 419 of the input-coupler 414 such that the k-vector of the grating 419 at the region labeled 420 is shifted sufficiently from the k-vector at the region labeled 418. This preferably results in the peak of the efficiency curve being shifted in angle sufficiently so as to significantly reduce the amount of infrared light that is diffracted out of the waveguide (i.e., is outcoupled) at the region labeled 420 and other regions of the input-coupler 414. Additionally, the grating period (i.e., the distance between adjacent grating planes), and thus the grating frequency (which is the reciprocal of the grating period), is varied between the lower boundary 415 and upper boundary 416 of each of the electronically switchable diffraction gratings 419 of the input-coupler 414 to achieve the desired combination of wedge and lens power.

More specifically, in accordance with certain embodiments, each of the electronically switchable diffraction gratings 419 of the input-coupler 414 has a k-vector angle at its lower boundary 415 that is greater than a k-vector angle at its upper boundary 416, with k-vector angles of the between the lower and upper boundaries 415, 416 gradually decreasing. Such a diffraction grating 419 can be said to have a varying k-vector, or a rolled k-vector. By varying the k-vector angle of the diffraction grating 419 along the direction the infrared light is propagated in the waveguide 412, efficient coupling of the infrared light into the waveguide 412 is achieved in a manner that causes most (and preferably all or significantly all) of the infrared light that is coupled into the waveguide 412 to be transmitted up the waveguide 412 by total internal reflections at which point the infrared light is outcoupled by the output-coupler 424.

In accordance with certain embodiments, each of the electronically switchable diffraction gratings 419 of the input-coupler 414 has a grating period (which can also be referred to as a grating spacing) at its lower boundary 415 that is less than the grating period at its upper boundary 416, with the grating period between the lower and upper boundaries 415, 416 gradually increasing. Such a diffraction grating can be said to have a varying grating period. This is the same as saying that each of the electronically switchable diffraction gratings 419 of the input-coupler 414 has a grating frequency at its lower boundary 415 that is greater than the grating frequency at its upper boundary 416, with the grating frequency between the lower and upper boundaries 415, 416 gradually decreasing. Such an electronically switchable diffraction gratings 419 of the input-coupler 414 can be said to have a varying grating frequency.

In an embodiment, the lens power and the wedge power of each electronically switchable diffraction gratings 419 of the input-coupler 414 are achieved by varying the grating frequency. The lens power focuses light from the eye plane. When the eye relief (distance from the eye pupil plane to the input diffraction grating) is equal to the diffractive lens focal length, the light is collimated by the lens power. The wedge power component diffracts this collimated light so that the minimum diffraction angle in the substrate is beyond the critical angle for total internal reflection (TIF) within the substrate and will therefore be guided within the waveguide. Light incident on a lower portion of the input-coupler 414 (near the lower boundary 415) is diffracted at a greater angle than the light incident on an upper portion (near the upper boundary 416) and progresses due to the combination of the lens power and the wedge power of the electronically switchable diffraction gratings 419 of the input-coupler 414. Since the input angles for peak efficiency are all substantially the same, it follows that the first beam of the construction optics for a diffraction grating 419 of input-coupler 414 will be near parallel. Since the diffractive power is varying according to the combination of the diffractive lens power and wedge power it follows that the second construction beam for the diffraction recording will be substantially convergent. The combination of these two beams provides a diffraction grating whereby the k-vector is naturally varying, in accordance with an embodiment. Preferably, the two construction beams are optimized such that the diffraction efficiency and diffractive power are optimized to meet the efficiency and geometric properties of the input-coupler 414.

The table below illustrates exemplary k-vector angles, and grating periods and frequencies of such an electronically switchable diffraction grating 419 of the input-coupler 414 where the total distance between the lower boundary 415 and the upper boundary 416 is 16 mm.

| Distance from lower boundary of diffraction grating (mm) | Ang. of Incidence (degrees) | Diffraction Angle (degrees) | K-vector angle (degrees) | grating period (um) | grating frequency (lines/um) |
|---|---|---|---|---|---|
| 0 | 0 | 71.4 | 125.7 | 0.427948438 | 2.3367301 |
| 1 | 0 | 67.85 | 123.925 | 0.447450853 | 2.2348823 |
| 2 | 0 | 64.75 | 122.375 | 0.466377182 | 2.1441872 |
| 3 | 0 | 61.95 | 120.975 | 0.485220537 | 2.0609185 |
| 4 | 0 | 59.3 | 119.65 | 0.504801536 | 1.9809765 |
| 5 | 0 | 56.8 | 118.4 | 0.525048022 | 1.9045877 |
| 6 | 0 | 54.45 | 117.225 | 0.545864943 | 1.831955 |
| 7 | 0 | 52.2 | 116.1 | 0.567636544 | 1.7616907 |
| 8 | 0 | 50.05 | 115.025 | 0.590348649 | 1.6939143 |
| 9 | 0 | 48 | 114 | 0.613973573 | 1.6287346 |
| 10 | 0 | 46.1 | 113.05 | 0.637812749 | 1.5678583 |
| 11 | 0 | 44.25 | 112.125 | 0.663055369 | 1.5081697 |
| 12 | 0 | 42.5 | 111.25 | 0.689015842 | 1.4513454 |
| 13 | 0 | 40.85 | 110.425 | 0.715584986 | 1.3974581 |
| 14 | 0 | 39.25 | 109.625 | 0.743534883 | 1.3449268 |
| 15 | 0 | 37.7 | 108.85 | 0.772924733 | 1.293787 |
| 16 | 0 | 36.2 | 108.1 | 0.803812347 | 1.2440715 |

In the above table, for simplicity and consistency, it is assumed that there is a zero degree angle of incidence of the infrared light beam incident on an electronically switchable diffraction grating of the input-coupler 414. However, that need not be the case and embodiments described herein are not limited to that condition.

Figure 4D:
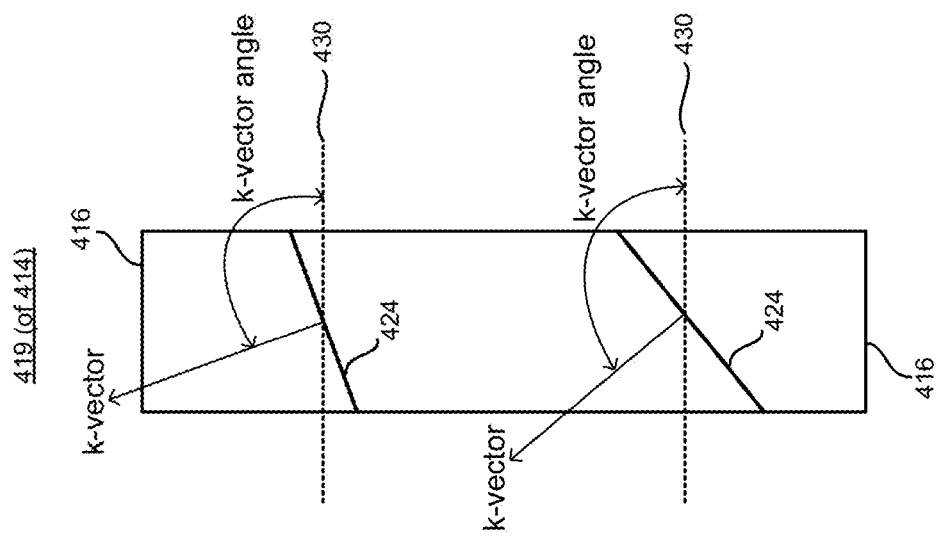
FIG. 4D illustrates exemplary k-vectors and corresponding exemplary k-vector angels of a diffraction grating of an input-coupler of a waveguide.

K-vectors of a diffraction grating are, by definition, normal to (i.e., perpendicular to) the fringe planes of the diffraction grating. The term k-vector angle, as used herein, refers to the angle of a k-vector relative to the surface normal of the diffraction grating, as can be appreciated from FIG. 4D. Referring to FIG. 4D, shown therein are two fringe planes 424 (of numerous fringe planes, the others of which are not shown). Also shown in FIG. 4D are dashed lines 430 which are normal to the surface of the diffraction grating. Two k-vectors are also shown, each of which is perpendicular to a respective fringe plane 424, and each of which has a different k-vector angle relative to the surface normal of the diffraction grating.

As noted above, in accordance with certain embodiments each of the electronically switchable diffraction gratings 419 of the input-coupler 414 has a rolled k-vector, where the k-vector angle at its lower boundary 415 is greater than the k-vector angle at its upper boundary 416, with k-vector angles of the between the lower and upper boundaries 415, 416 gradually decreasing. The use of such a rolled k-vector, in combination with a narrow ABW, beneficially helps to substantially maximize the amount of reflected infrared light that reaches the eye tracking IR sensor 134B. The rolled k-vector also helps to reduce the amount of chromatic flare that may undesirably produce a rainbow effect that is viewable by the wearer of a head mounted display device (e.g., the device 2) that includes the waveguide 412. Experiments have shown that if an input-coupler has a high ABW, a rainbow effect may be visible when broad spectral lighting (e.g., produced by the sun or tungsten bulbs) enters the input-coupler and is diffracted into waveguide mode. The diffraction angle of such broad spectral lighting is different for each different wavelength of the light, as specified by the diffraction equation. Some of the beams of light that enter the waveguide at the input-coupler are incident on the input-coupler one or more additional times as the beams propagate within the waveguide toward the output-coupler. Some of this light may be diffracted out of the waveguide in the direction of the user's eye. Since the spacing between fringe planes of the diffraction grating varies along the length of the waveguide, the diffraction angles exiting the waveguide are different than the angles entering the waveguide. This can cause light (e.g., white light) to be split into multiple spectral lines which cause the rainbow effect. However, by using a narrow ABW, instead of a broad ABW, such a rainbow effect can be beneficially substantially eliminated. This mechanism is supported by holograms where the modulation of refractive index is low. This is contrary to what is generally desired of holograms that are used to display images, which are required to be high modulation holograms to support a relatively large field of view.

The eye motion box represents the area in which a user's eye 440 can move while still being within the field-of-view (FOV) of the input-coupler 414, and thus, within the FOV of the IR eye tracking sensor 134B. An exemplary size of the eye motion box is 16 mm×28 mm (vertical×horizontal). Each of the aforementioned electronically switchable diffractive gratings 419 can be used to image an entire eye motion box. Alternatively, an eye motion box can be split into multiple zones, such that a first electronically switchable diffractive grating 419 (or a first stack of electronically switchable diffractive gratings 419 arranged parallel to one another) is adjacent to a second electronically switchable diffractive grating 419 (or to a second stack of electronically switchable diffractive gratings 419 arranged parallel to one another), with the second electronically switchable diffractive grating 419 (or the second stack of electronically switchable diffractive gratings 419) providing a field-of-view that differs from the field-of-view provided by the first electronically switchable diffractive grating 419 (or the first stack of electronically switchable diffractive gratings 419).

The first and second electronically switchable diffractive gratings 419 can be arranged horizontally adjacent to one another such that each stack of electronically switchable diffractive gratings 419 images a horizontal half of the exemplary 16 mm×28 mm eye motion box, i.e., each images 8 mm×28 mm. Similarly, first and second stacks of electronically switchable diffractive gratings 419 can be arranged horizontally adjacent to one another such that each stack of electronically switchable diffractive gratings 419 images a horizontal half of the exemplary 16 mm×28 mm eye motion box, i.e., each images 8 mm×28 mm.

The first and second electronically switchable diffractive gratings 419 can alternatively be arranged vertically adjacent to one another such that each electronically switchable diffractive grating 419 images a vertical half of the exemplary 16 mm×28 mm eye motion box, i.e., each images 16 mm×14 mm. Similarly, first and second stacks of electronically switchable diffractive gratings 419 can be arranged vertically adjacent to one another such that each stack of electronically switchable diffractive gratings 419 can be used to image a vertical half of the exemplary 16 mm×28 mm eye motion box, i.e., each images 16 mm×14 mm.

It would also be possible to split the eye motion box into multiple horizontal zones and multiple vertical zones. For example, the eye motion box can be split into four zones and imaged using an input-coupler 414 including four electronically switchable diffractive gratings 419 (or stacks thereof) arranged in a two-by-two pattern. In addition to using multiple electronically switchable diffractive gratings 419 (or stacks thereof) to split the imaging of the eye motion box into multiple zones, multiple electronically switchable diffractive gratings 419 (or stacks thereof) can be used to increase the overall size of the eye motion box to accommodate for greater variations in inter-pupillary distance (IPD) and variations in other eye location and facial features.

More generally, two or more electronically switchable diffractive gratings 419 (or stacks thereof) of an input-coupler 414 can be arranged vertically one above the other. Alternatively, or additionally, two or more electronically switchable diffractive gratings 419 (or stacks thereof) can be arranged horizontally one beside the other. In such embodiments, the input-coupler controller 223 can control the multiple electronically switchable diffractive gratings 419 so that only one grating 419 is turned on at a time. In such embodiments, an eye may be imaged in multiple frames. It is also possible that the eye may be within the FOV of only one of the gratings 419, or stack thereof, and thus, can still be imaged in a single frame.

FIG. 4E illustrates an exemplary front view of a waveguide 412, which includes an input-coupler 414 and an output-coupler 424, wherein the input-coupler 414 includes an electronically switchable diffraction grating 419 (or a stack thereof). FIG. 4F illustrates how an eye motion box can be split into two zones by positioning two electronically switchable diffractive gratings, labeled 419a and 419b, (or stacks thereof) horizontally adjacent to one another. FIG. 4G illustrates how an eye motion box can be split into two zones by positioning two electronically switchable diffractive gratings, labeled 419a and 419b, (or stacks thereof) vertically adjacent to one another. FIG. 4H illustrates how an eye motion box can be split into four zones using a two-by-two tiling of electronically switchable diffractive gratings (or stacks thereof), labeled 419a, 419b, 419c and 419d. These are just a few examples how multiple electronically switchable diffractive gratings 419, or multiple stacks of electronically switchable diffractive gratings 419, of the input-coupler 414 can be arranged, which are not intended to be all encompassing.

In the embodiments described with reference to FIGS. 4F-4H, the input-coupler 414 includes a plurality of electronically switchable diffractive gratings 419 arranged relative to one another such that at least some of the electronically switchable diffractive gratings have different fields-of-view than one another. Each of the electronically switchable diffractive gratings 419 of the input-coupler 414, when turned on, receives infrared light and couples the received infrared light into the waveguide 412. In specific embodiment, the input-coupler controller 223 controls when each of the electronically switchable diffractive gratings 419 is turned on, such that only one of the electronically switchable diffractive gratings 419 is turned on at a time. The eye tracking IR sensor 134B images the eye in dependence on infrared light beams that exit the waveguide 412 at the output-coupler 424. In accordance with an embodiment, the image analysis module 225 analyzes images, obtained using the sensor, to determine which one or more of the electronically switchable diffractive gratings 419, when turned on, includes an eye or portion thereof within its field-of-view. If one of the gratings 419 includes the entire eye (or the entire portion of the eye of interest) within its field-of-view, then that grating 419 can thereafter be used for eye tracking. It is also possible that the eye (or the portion of the eye of interest) is partially within the field-of-view of more than one grating 419, in which case, images obtaining using more than one of the electronically switchable diffractive gratings 419 can be used for eye tracking.

The arranging of electronically switchable diffractive gratings (or stacks thereof) adjacent to one another in horizontal and/or vertical directions can be referred to as tiling. One reason for tiling the electronically switchable diffractive gratings (or stacks thereof) next to one another is to increase the eye motion box without decreasing the special resolution of images of the eye. For example, if the desire is to double the size of the eye motion box without increasing the resolution of the eye tracking IR sensor 134B, then the number of adjacent electronically switchable diffractive gratings (or stacks thereof) can be simply doubled. Conversely, such tiling can instead be used to decrease the resolution of the eye tracking IR sensor 134B by increasing the extent of the tiling. Another benefit of tiling the electronically switchable diffractive gratings (or stacks thereof) is that such tiling can be used to substantially avoid high angles of incidence within the waveguide.

Figure 5:
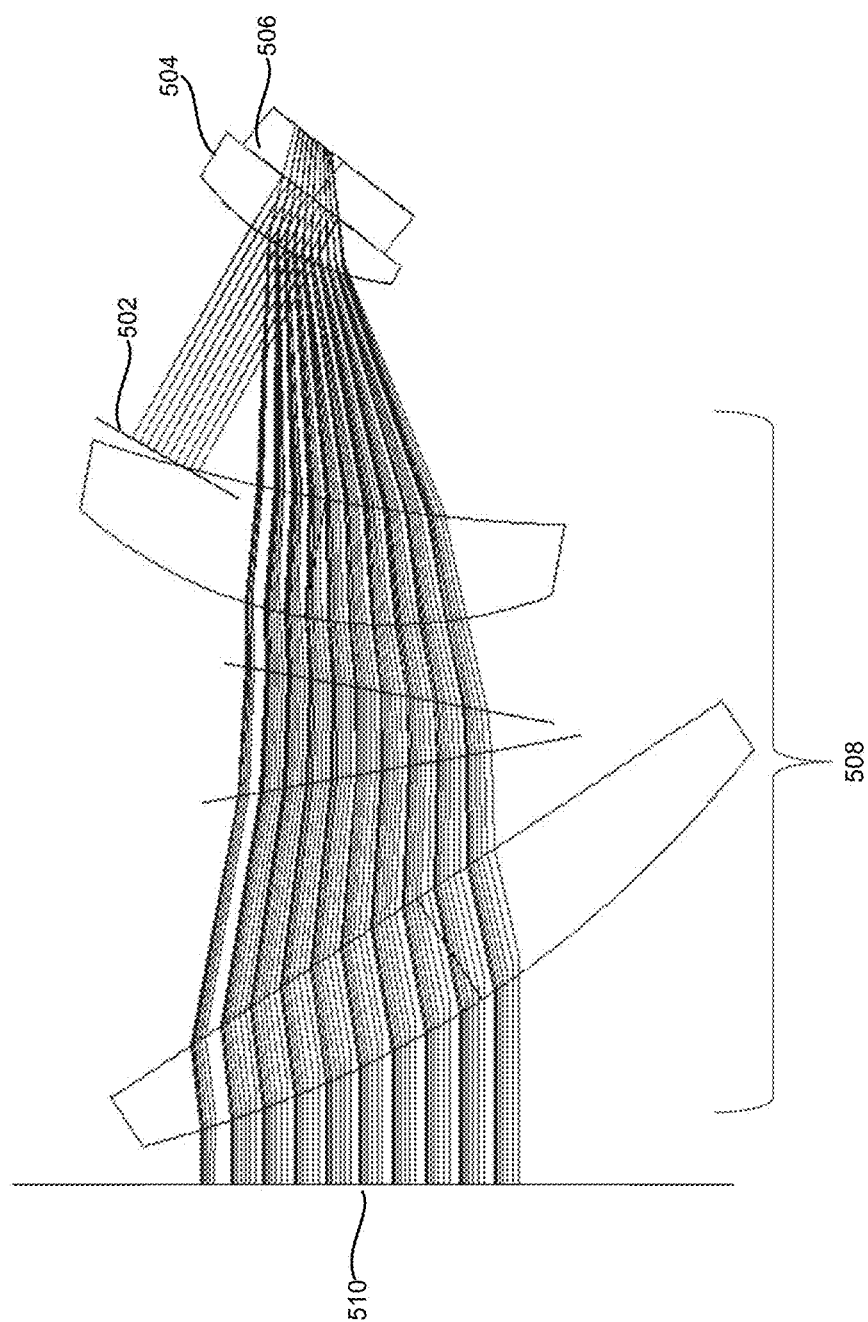
FIG. 5 illustrates how lens power and wedge power can be mathematically combined in a two beam process to generate a phase copy master hologram, which in turn can be used in a contact copy process to produce a diffraction grating type of input-coupler according to an embodiment.

FIG. 5 illustrates how lens power and wedge power can be combined in a two beam process to generate a master hologram, which in turn can be used in a contact copy process to produce a diffraction grating 419 of the input-coupler 414. Referring to FIG. 5, shown therein is a first surface 502, a cover lens 504, a holographic recording medium 506 that is used to generate the master hologram being recorded, an off-axis lens system 508, and a second surface 510. The holographic recording medium 506 can be a dichromated gelatin or a photopolymer, but is not limited thereto. A first beam is generated by a collimated beam emanating from the first surface 502. The first beam is converged by a cover lens 504 before it is incident on the recording medium 506. A second beam is generated by a collimated beam emanating from the second surface 510. This beam is modified by the off-axis lens system 508 and the cover lens 504 before being incident on the recording medium. These two beams interfere with one another to produce an interference pattern in the holographic recording medium 506 to thereby generate the master hologram. Such a master hologram can then be used to mass produce diffraction gratings 419 of the input-coupler 414 using contact copying. The lens or diffractive power of the contact copy will only be the same if the master hologram is in direct contact with the copy. Where there is a gap or distance between the master and the copy, the master hologram should be designed to compensate for this gap.

Figure 6:
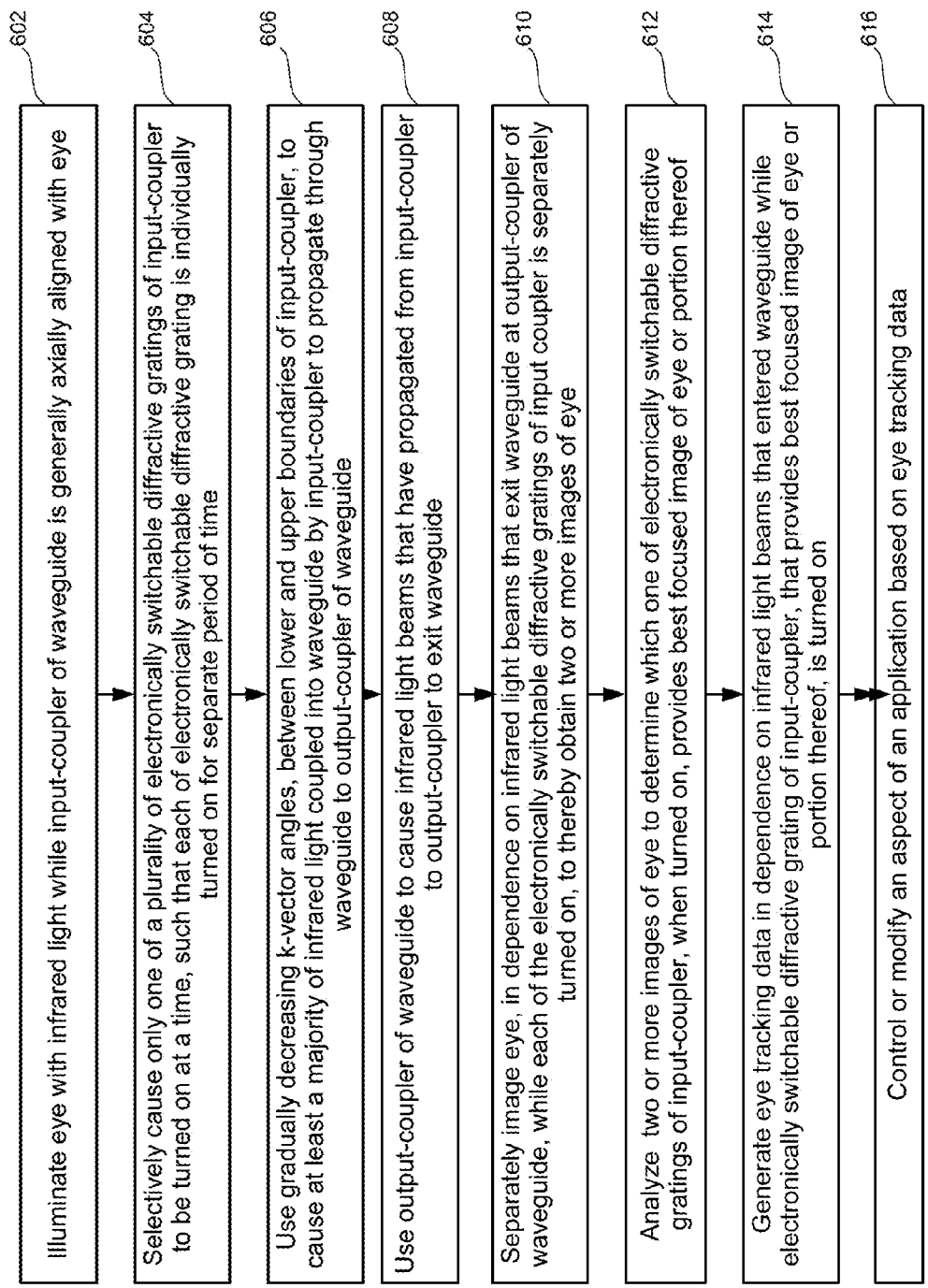
FIG. 6 is a high level flow diagram that is used to summarize a method for use in tracking an eye.

FIG. 6 is a flowchart that is used to summarize a method for use in eye tracking. Referring to FIG. 6, at step 602, an eye is illuminated with infrared light while an input-coupler of a waveguide is generally axially aligned with the eye. In accordance with specific embodiments, described above with reference to FIG. 4C, the input-coupler includes a stack of two or more electronically switchable diffractive gratings arranged parallel to one another. Each of the electronically switchable diffractive gratings having a respective lens power and a respective prismatic power, with the lens power of each of the electronically switchable diffractive gratings differing from one another such that each of the electronically switchable diffractive gratings has a different focal length.

Still referring to FIG. 6, step 604 involves selectively causing only one of the electronically switchable diffractive gratings of the input-coupler to be turned on at a time, such that each of the electronically switchable diffractive gratings is individually turned on for a separate period of time. Step 606 involves using gradually decreasing k-vector angles, between lower to upper boundaries of the input-coupler, to cause at least a majority of (and preferably all or significantly all of) the infrared light that is coupled into the waveguide by the input-coupler to propagate within the waveguide to an output-coupler of the waveguide. Step 606, or a separate step, can also involve using an angular bandwidth of the input-coupler that is equal to or less than 5 degrees to limit an extent that different infrared light beams, coupled into the waveguide after being reflected from a same point on the eye, can be non-collimated as the different infrared light beams propagate from the input-coupler to the output-coupler. As indicated at step 608, the output-coupler of the waveguide is used to cause the infrared light beams that have propagated from the input-coupler to the output-coupler to exit the waveguide.

Step 610 involves separately imaging the eye, in dependence on infrared light beams that exit the waveguide at an output-coupler of the waveguide, while each of the electronically switchable diffractive gratings of the input coupler is separately turned on, to thereby obtain two or more images of the eye. For example, where the input-coupler includes a stack of four electronically switchable diffractive gratings arranged parallel to one another, each of which has its own focal length, as in FIG. 4B, then four images of the eye can be obtained at step 610.

Step 610 involves analyzing the two or more images of the eye to determine which one of the electronically switchable diffractive gratings of the input-coupler, when turned on, provides a best focused image of the eye or portion thereof. The term best, as used herein, is a relative term that is not intended to refer to an optimum. In other words, the best focused image, of a plurality of images, is not necessarily a perfectly focused image. Rather, the best focused image is the one of the plurality of images that is more in-focus than other images. In accordance with specific embodiments, described in additional detail above, step 610 can include determining a measure of at least one of resolution, contrast, or entropy of each of the two or more images to thereby determine a metric of focus for each of the two or more image. Step 610 can also include determining which one of the two or more images has a greatest metric of focus, and selecting the one of the electronically switchable diffractive gratings of the input-coupler that was used to obtain the image having the greatest metric of focus as the electronically switchable diffractive grating that provides the best focused image of the eye or portion thereof.

Step 614 involves generating eye tracking data in dependence on infrared light beams that entered the waveguide while the electronically switchable diffractive grating of the input-coupler, that provides the best focused image of the eye or portion thereof, is turned on. Step 616 involves controlling or modifying an aspect of an application based on the eye tracking data. More generally, eye tracking is performed using one or more images of the eye obtained while the electronically switchable diffractive grating of the input-coupler, that provides the best focused image of the eye or portion thereof, is turned on. As was explained above, this can be achieved using an eye tracking IR sensor (e.g., 134B). The sensor can be, e.g., a charge-coupled device (CCD) or CMOS pixel sensor array, but is not limited thereto. Some examples of eye tracking data are image data from an infrared camera or positions detected for glints by a position sensitive detector (PSD). Eye tracking data can be used, for example, to determine a point of gaze, which indicates one or more objects, real or virtual, at which a user is gazing. In other words, eye tracking data can be used to determine a direction or object at which the user is looking. Eye tracking, as is known in the art, can involve measuring vergence, inter-pupillary distance (IPD), gaze determination, eye movement based commands, biometric identification, but is not limited thereto.

The position of the pupil within the eye socket can be identified by known imaging techniques when the IR sensor is an IR camera, or using a type of position sensitive detector (PSD). For a more specific example, the position of the pupil can be identified by known imaging techniques which detects the reflection from the retina when the IR illumination is substantially on-axis. In this embodiment the light reflecting from the retina is brighter than the light reflecting from the surrounding iris. This embodiment is generally called a bright pupil method of eye tracking. In another embodiment, the IR illumination is substantially off axis. In this embodiment, the light entering the eye pupil does not get reflected by the retina back into the IR camera. In this case, the light inside the pupil reaching the IR camera is much less than the light reflected from the iris back into the IR camera. This embodiment is generally known as the dark pupil method. Other reflections from the eye, such as the so called Purkinje reflections from the cornea, can be imaged by the camera to enable calculation of an eye vector. The reflections from the cornea generally form small spots on the IR camera. These reflections are sometimes called eye glints. It can be shown that the eye vector can be calculated by tracking the relative positions of the pupil and glints. These are known image processing techniques, e.g., as disclosed in U.S. Pat. No. 7,401,920, entitled "Head Mounted Eye Tracking and Display System", issued Jul. 22, 2008 to Kranz et al. Such techniques can locate a position of the center of the eye relative to a tracking camera (e.g., eye tracking IR sensor 134B). Generally, eye tracking involves obtaining an image of the eye and using computer vision techniques to determine the location of the pupil within the eye socket. In one embodiment, it is sufficient to track the location of one eye since the eyes usually move in unison. However, it is also possible to track each eye separately. Where two eyes are being tracked, there can be a separate one of the waveguides 412 described herein for each one of the eyes. Another example of a patent that describes techniques for tracking an eye based on reflected infrared light and generating eye tracking data is U.S. Pat. No. 8,487,838, entitled "Gaze Detection in a See-Through, Near-Eye, Mixed Reality Display," issued Jul. 16, 2013, to Lewis et al.

Step 616 can be performed, e.g., using a processor (e.g., 210 or 320). Step 616 can involve, for example, enabling a user to make a selection from a list, enabling a user to control how an avatar proceeds through a virtual environment, or causing certain virtual objects to be emphasized, but are not limited thereto. Step 616 can additionally, or alternatively, involve observing a user's reactions to certain visual stimuli, or the like.

The waveguides disclosed herein advantageously can be employed with eye tracking hardware in a manner that does not impair the see-through properties of the mixed reality display device system. Further, the waveguides disclosed herein enables imaging of the eye that works with all types of prescription spectacles, and enables imaging of the eye that covers the entire eye movement range plus an interpupillary distance range.

In the Figures, the waveguide 412 was typically shown as being a waveguide that includes a pair of planar surfaces. In an alternative embodiment, surfaces of the waveguide could be non-planar, i.e., curved. While gratings may be more easily manufacture on or in planar surfaces, with curved surface(s) it could be possible to reduce some of the aberrations in the system.

Certain embodiments described herein are directed to an apparatus for use in tracking an eye that is illuminated by infrared light having an infrared wavelength. The output-coupler can be a linear grating, a holographic grating or a prism, but is not limited thereto. In certain embodiments, the input-coupler includes a stack of two or more electronically switchable diffractive gratings arranged parallel to one another. Each of the electronically switchable diffractive gratings has a respective lens power and a respective prismatic power. The lens power of each of the electronically switchable diffractive gratings differ from one another such that each of the electronically switchable diffractive gratings has a different focal length. Each of the electronically switchable diffractive gratings, when turned on, is adapted to receive infrared light having the infrared wavelength and couple the received infrared light into the waveguide. Each of the electronically switchable diffractive gratings includes a lower boundary and an upper boundary, the upper boundary being closer to the output-coupler than the lower boundary. In an embodiment, each of the electronically switchable diffractive gratings has a k-vector angle at the lower boundary that is greater than a k-vector angle of the electronically switchable diffractive gratings at the upper boundary, with k-vector angles between the lower and upper boundaries gradually decreasing as distances decrease between grating planes of the electronically switchable diffractive gratings and the upper boundary.

When the input-coupler is positioned in front of an eye that is illuminated with the infrared light, at least portion of the infrared light reflected from the eye and received by the input-coupler is coupled into the waveguide at the input-coupler, propagates within the waveguide from the input-coupler to the output-coupler by way of total internal reflections, and exits the waveguide proximate the output-coupler. A sensor images an eye in dependence on infrared light beams that exit the waveguide at the output-coupler. In certain embodiments, a lens module is between the output-coupler and the sensor, and the infrared light beams that exit the waveguide at the output-coupler pass through the lens module before being incident on the sensor.

An input-coupler controller controls when each of the electronically switchable diffractive gratings is turned on, such that only one of the electronically switchable diffractive gratings is turned on at a time. An image analyzer analyzes two or more images of an eye, obtained using the sensor, to determine which one of the electronically switchable diffractive gratings, when turned on, provides a best focused image of an eye or portion thereof. The input-coupler controller causes the one of the electronically switchable diffractive gratings, which the image analysis module determines provides the best focused image of the eye, to be used for imaging the eye during eye tracking.

In certain embodiments, the input-coupler also includes a second stack of two or more electronically switchable diffractive gratings arranged parallel to one another, wherein the second stack being adjacent to the first stack. In such an embodiment, the electronically switchable diffractive gratings in the second stack provide a field-of-view that differs from the field-of-view provided by the electronically switchable diffractive gratings in the first stack. Further, in such an embodiment, the image analysis module can determine which one of the electronically switchable diffractive gratings, when turned on, includes an eye within its field-of-view and provides a sharpest image of an eye or portion thereof.

Certain embodiments described herein are directed to a method for use in tracking an eye. Such a method includes illuminating an eye with infrared light while an input-coupler of a waveguide is generally axially aligned with the eye. The input-coupler includes a stack of two or more electronically switchable diffractive gratings arranged parallel to one another, each having a respective lens power and a respective prismatic power, the lens power of each of the electronically switchable diffractive gratings differing from one another such that each of the electronically switchable diffractive gratings has a different focal length. The method can also include selectively causing only one of the electronically switchable diffractive gratings of the input coupler to be turned on at a time, such that each of the electronically switchable diffractive gratings is individually turned on for a separate period of time. Additionally, the method can include separately imaging the eye, in dependence on infrared light beams that exit the waveguide at an output-coupler of the waveguide, while each of the electronically switchable diffractive gratings of the input coupler is separately turned on, to thereby obtain two or more images of the eye. Further, the method can include analyzing the two or more images of the eye to determine which one of the electronically switchable diffractive gratings of the input-coupler, when turned on, provides a best focused image of the eye or portion thereof. Thereafter, eye tracking can be performed using one or more images of the eye obtained while the electronically switchable diffractive grating of the input-coupler, that provides the best focused image of the eye or portion thereof, is turned on.

In accordance with an embodiment, the input-coupler of a waveguide includes two or more electronically switchable diffractive gratings arranged relative to one another such that the two or more electronically switchable diffractive gratings have different fields-of-view from one another. In this embodiment, each of the electronically switchable diffractive gratings of the input-coupler, when turned on, is adapted to receive infrared light having the infrared wavelength and couple the received infrared light into the waveguide. An input-coupler controller controls when each of the electronically switchable diffractive gratings is turned on, such that only one of the electronically switchable diffractive gratings is turned on at a time. A sensor images an eye in dependence on infrared light beams that exit the waveguide at the output-coupler. When the input-coupler is positioned in front of an eye that is illuminated with the infrared light, at least portion of the infrared light reflected from the eye and received by the input-coupler is coupled into the waveguide at the input-coupler, propagates within the waveguide from the input-coupler to the output-coupler by way of total internal reflections, and exits the waveguide proximate the output-coupler. An image analysis module analyzes images, obtained using the sensor, to determine which one or more of the electronically switchable diffractive gratings, when turned on, includes an eye (or portion thereof of interest) within its field-of-view. A processor generates eye tracking data in dependence one or more images of the eye, and controls or modifies an aspect of an application based on the eye tracking data.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the present technology. For example, it would be possible to combine or separate some of the steps shown in FIG. 6. For another example, it is possible to change the boundaries of some of the blocks shown in FIGS. 3A and 3B.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. It is intended that the scope of the technology be defined by the claims appended hereto.

What is claimed is:

1. An apparatus for use in tracking an eye that is illuminated by infrared light having an infrared wavelength, the apparatus comprising:
a waveguide that is transparent and includes an input-coupler and an output-coupler;
the input-coupler comprising a stack of two or more electronically switchable diffractive gratings arranged parallel to one another;
wherein each of the electronically switchable diffractive gratings has a respective lens power and a respective prismatic power;
wherein the lens power of each of the electronically switchable diffractive gratings differ from one another such that each of the electronically switchable diffractive gratings has a different focal length; and
wherein each of the electronically switchable diffractive gratings, when turned on, is adapted to receive infrared light having the infrared wavelength and couple the received infrared light into the waveguide.

2. The apparatus of claim 1, wherein:
each of the electronically switchable diffractive gratings includes a lower boundary and an upper boundary, the upper boundary being closer to the output-coupler than the lower boundary; and
each of the electronically switchable diffractive gratings has a k-vector angle at the lower boundary that is greater than a k-vector angle of the electronically switchable diffractive gratings at the upper boundary, with k-vector angles between the lower and upper boundaries gradually decreasing as distances decrease between grating planes of the electronically switchable diffractive gratings and the upper boundary.

3. The apparatus of claim 1, wherein when the input-coupler is positioned in front of an eye that is illuminated with the infrared light, at least a portion of the infrared light reflected from the eye and received by the input-coupler is coupled into the waveguide at the input-coupler, propagates within the waveguide from the input-coupler to the output-coupler by way of total internal reflections, and exits the waveguide proximate the output-coupler.

4. The apparatus of claim 1, further comprising:
a sensor that images an eye in dependence on infrared light beams that exit the waveguide at the output-coupler;
an input-coupler controller that controls when each of the electronically switchable diffractive gratings is turned on, such that only one of the electronically switchable diffractive gratings is turned on at a time; and
an image analyzer that analyzes two or more images of an eye, obtained using the sensor, to determine which one of the electronically switchable diffractive gratings, when turned on, provides a best focused image of an eye or portion thereof.

5. The apparatus of claim 4, wherein:
the input-coupler controller causes the one of the electronically switchable diffractive gratings, which the image analysis module determines provides the best focused image of the eye, to be used for imaging the eye during eye tracking.

6. The apparatus of claim 5, further comprising:
a lens module between the output-coupler and the sensor;
wherein infrared light beams that exit the waveguide at the output-coupler pass through the lens module before being incident on the sensor.

7. The apparatus of claim 1, wherein:
the input-coupler comprises a second stack of two or more electronically switchable diffractive gratings arranged parallel to one another, the second stack being adjacent to the first stack, and the electronically switchable diffractive gratings in the second stack providing a field-of-view that differs from the field-of-view provided by the electronically switchable diffractive gratings in the first stack.

8. The apparatus of claim 7, further comprising:
a sensor that images an eye in dependence on infrared light beams that exit the waveguide at the output-coupler; and
an input-coupler control module that controls when each of the electronically switchable diffractive gratings in the first and second stacks is turned on, such that only one of the electronically switchable diffractive gratings is turned on at a time;
an image analysis module that analyzes images, obtained using the sensor, to determine which one of the electronically switchable diffractive gratings, when turned on, includes an eye within its field-of-view and provides a sharpest image of an eye or portion thereof.

9. The apparatus of claim 1, wherein each of the electronically switchable diffractive gratings has a grating period at its lower boundary that is less than the grating period at its upper boundary, with the grating period between the lower and upper boundaries gradually increasing.

10. The apparatus of claim 1, wherein each of the electronically switchable diffractive gratings comprises an electronically switchable Bragg grating (ESBG), an electronically switchable lithium niobate diffraction grating or an electronically switchable polymer liquid crystal polymer slices (POLYCRYPS) diffraction grating.

11. A method for use in tracking an eye, the method comprising:
illuminating an eye with infrared light while an input-coupler of a waveguide is generally axially aligned with the eye, the input-coupler comprising a stack of two or more electronically switchable diffractive gratings arranged parallel to one another, each of the electronically switchable diffractive gratings having a respective lens power and a respective prismatic power, the lens power of each of the electronically switchable diffractive gratings differing from one another such that each of the electronically switchable diffractive gratings has a different focal length;
selectively causing only one of the electronically switchable diffractive gratings of the input coupler to be turned on at a time, such that each of the electronically switchable diffractive gratings is individually turned on for a separate period of time;
separately imaging the eye, in dependence on infrared light beams that exit the waveguide at an output-coupler of the waveguide, while each of the electronically switchable diffractive gratings of the input coupler is separately turned on, to thereby obtain two or more images of the eye; and
analyzing the two or more images of the eye to determine which one of the electronically switchable diffractive gratings of the input-coupler, when turned on, provides a best focused image of the eye or portion thereof.

12. The method of claim 11, further comprising:
performing eye tracking using one or more images of the eye obtained while the electronically switchable diffractive grating of the input-coupler, that provides the best focused image of the eye or portion thereof, is turned on.

13. The method of claim 11, further comprising:
generating eye tracking data in dependence on infrared light beams that entered the waveguide while the electronically switchable diffractive grating of the input-coupler, that provides the best focused image of the eye or portion thereof, is turned on; and
controlling or modifying an aspect of an application based on the eye tracking data.

14. The method of claim 11, wherein the analyzing comprises:
determining a measure of at least one of resolution, contrast, or entropy of each of the two or more images to thereby determine a metric of focus for each of the two or more images;
determining which one of the two or more images has a greatest metric of focus; and
selecting the one of the electronically switchable diffractive gratings of the input-coupler that was used to obtain the image having the greatest metric of focus as the electronically switchable diffractive grating that provides the best focused image of the eye or portion thereof.

15. The method of claim 11, further comprising:
using gradually decreasing k-vector angles, between lower to upper boundaries of each of the electronically switchable diffractive gratings of input-coupler, to cause at least a majority of the infrared light that is coupled into the waveguide by the input-coupler to propagate through the waveguide to the output-coupler of the waveguide; and using the output-coupler of the waveguide, causing the infrared light beams that have propagated from the input-coupler to the output-coupler to exit the waveguide.

16. An apparatus for use in tracking an eye that is illuminated by infrared light having an infrared wavelength, the apparatus comprising:
a waveguide that is transparent and includes an input-coupler and an output-coupler,
the input-coupler comprising two or more electronically switchable diffractive gratings arranged relative to one another such that the two or more electronically switchable diffractive gratings have different fields-of-view than one another, and
each of the electronically switchable diffractive gratings of the input-coupler, when turned on, adapted to receive infrared light having the infrared wavelength and couple the received infrared light into the waveguide;
an input-coupler controller that controls when each of the electronically switchable diffractive gratings is turned on, such that only one of the electronically switchable diffractive gratings is turned on at a time;
a sensor that images an eye in dependence on infrared light beams that exit the waveguide at the output-coupler; and
an image analysis module that analyzes images, obtained using the sensor, to determine which one or more of the electronically switchable diffractive gratings, when turned on, includes the eye or a portion thereof within its field-of-view.

17. The apparatus of claim 16, wherein when the input-coupler is positioned in front of an eye that is illuminated with the infrared light, at least a portion of the infrared light reflected from the eye and received by the input-coupler is coupled into the waveguide at the input-coupler, propagates within the waveguide from the input-coupler to the output-coupler by way of total internal reflections, and exits the waveguide proximate the output-coupler.

18. The apparatus of claim 16, further comprising:
a processor that generates eye tracking data in dependence one or more images of the eye obtained using the sensor, and controls or modifies an aspect of an application based on the eye tracking data.

19. The apparatus of claim 16, wherein:
each of the electronically switchable diffractive gratings includes a lower boundary and an upper boundary, the upper boundary being closer to the output-coupler than the lower boundary; and
each of the electronically switchable diffractive gratings has a k-vector angle at the lower boundary that is greater than a k-vector angle of the electronically switchable diffractive gratings at the upper boundary, with k-vector angles between the lower and upper boundaries gradually decreasing as distances decrease between grating planes of the electronically switchable diffractive gratings and the upper boundary.

20. The apparatus of claim 16, wherein:
if the image analysis module determines that a portion of the eye that is of interest for eye tracking is entirely within the field-of-view of a single one of the electronically switchable diffractive gratings, then the input-coupler controller causes the single one of the electronically switchable diffractive gratings to be used for imaging the eye during eye tracking;
if the image analysis module determines that the portion of the eye that is of interest for eye tracking is partially within the field-of-view of at least two different ones of the electronically switchable diffractive gratings, then the input-coupler controller causes the at least two different ones of the electronically switchable diffractive gratings to be used for imaging the eye during eye tracking; and
the portion of the eye that is of interest for eye tracking is predetermined and can be the entire eye or just a portion thereof.

* * * * *